United States Patent
Gross et al.

(10) Patent No.: US 9,649,487 B2
(45) Date of Patent: May 16, 2017

(54) ENHANCING PERFUSION BY CONTRACTION

(71) Applicants: Yossi Gross, Moshav Mazor (IL); Amir Dagan, Kibbutz Megiddo (IL); Yotam Reisner, Kiryat Tivon (IL); Offer Glasberg, Zichron Ya'akov (IL); Nitai Hanani, Haifa (IL); Gal Ariav, Givaat Ada (IL)

(72) Inventors: Yossi Gross, Moshav Mazor (IL); Amir Dagan, Kibbutz Megiddo (IL); Yotam Reisner, Kiryat Tivon (IL); Offer Glasberg, Zichron Ya'akov (IL); Nitai Hanani, Haifa (IL); Gal Ariav, Givaat Ada (IL)

(73) Assignee: ENOPACE BIOMEDICAL LTD., Caesarea Industrial Park (IL)

( * ) Notice: Subject to any disclaimer, the term of this patent is extended or adjusted under 35 U.S.C. 154(b) by 0 days.

(21) Appl. No.: 13/968,868

(22) Filed: Aug. 16, 2013

(65) Prior Publication Data
US 2013/0338748 A1    Dec. 19, 2013

Related U.S. Application Data

(63) Continuation of application No. 12/851,214, filed on Aug. 5, 2010, now Pat. No. 8,538,535.

(51) Int. Cl.
*A61N 1/05*     (2006.01)
*A61N 1/36*     (2006.01)
(Continued)

(52) U.S. Cl.
CPC .............. *A61N 1/05* (2013.01); *A61N 1/056* (2013.01); *A61N 1/0514* (2013.01);
(Continued)

(58) Field of Classification Search
CPC ...................................................... A61N 1/056
See application file for complete search history.

(56) References Cited

U.S. PATENT DOCUMENTS 3,650,277 A    3/1972  Sjostrand et al.
3,661,148 A    5/1972  Kolin
(Continued)

FOREIGN PATENT DOCUMENTS

EP    0 109 935    5/1984
EP    0791341      2/1996
(Continued)

OTHER PUBLICATIONS

Extended European Search Report dated Oct. 31, 2013 which issued during the prosecution of Applicant's European App No. 11814203.3.
(Continued)

*Primary Examiner* — Eric D. Bertram
(74) *Attorney, Agent, or Firm* — Sughrue Mion, PLLC

(57) ABSTRACT

Apparatus and methods are described including a mechanical support element that is placed inside a first vein of a subject. At least one electrode disposed on the mechanical support element is placed inside the first vein, in a vicinity of a site upstream of a bifurcation with a second vein of the subject. A control unit enhances downstream blood flow from the first vein by driving the at least one electrode to divert blood downstream into the second vein by constricting the first vein at the upstream site, by driving the at least one electrode to apply a current to the vicinity of the site. The mechanical support element prevents the first vein from collapsing by providing mechanical support to the vein. Other embodiments are also described.

5 Claims, 11 Drawing Sheets

(51) Int. Cl.
    *A61F 2/82*         (2013.01)
    *A61N 1/365*        (2006.01)
(52) U.S. Cl.
    CPC ............ *A61N 1/0521* (2013.01); *A61N 1/36*
               (2013.01); *A61F 2/82* (2013.01); *A61N*
                                    *1/36564* (2013.01)

(56) References Cited

U.S. PATENT DOCUMENTS

| | | |
|---|---|---|
| 4,154,227 A | 5/1979 | Krause et al. |
| 4,201,219 A | 5/1980 | Bozal Gonzalez |
| 4,474,630 A | 10/1984 | Planck et al. |
| 4,692,148 A | 9/1987 | Kantrowitz et al. |
| 4,791,931 A | 12/1988 | Slate |
| 4,809,681 A | 3/1989 | Kantrowitz et al. |
| 4,821,723 A | 4/1989 | Baker et al. |
| 4,848,352 A | 7/1989 | Pohndorf |
| 4,938,766 A | 7/1990 | Jarvik |
| 5,192,271 A | 3/1993 | Kalb et al. |
| 5,199,428 A | 4/1993 | Obel et al. |
| 5,224,491 A | 7/1993 | Mehra |
| 5,265,011 A | 11/1993 | O'Rourke et al. |
| 5,265,601 A | 11/1993 | Mehra |
| 5,306,292 A | 4/1994 | Lindegren |
| 5,324,323 A | 6/1994 | Bui |
| 5,330,507 A | 7/1994 | Schwartz |
| 5,372,573 A | 12/1994 | Habib |
| 5,411,031 A | 5/1995 | Yomtov |
| 5,423,871 A | 6/1995 | Hoegnelid et al. |
| 5,458,626 A | 10/1995 | Krause |
| 5,487,760 A | 1/1996 | Villafana |
| 5,540,730 A | 7/1996 | Terry et al. |
| 5,571,150 A | 11/1996 | Wernicke et al. |
| 5,612,314 A | 3/1997 | Stamler |
| 5,645,839 A | 7/1997 | Chobanian et al. |
| 5,649,966 A | 7/1997 | Noren et al. |
| 5,651,378 A | 7/1997 | Matheny et al. |
| 5,669,924 A | 9/1997 | Shaknovich |
| 5,690,681 A | 11/1997 | Geddes et al. |
| 5,707,400 A | 1/1998 | Terry, Jr. et al. |
| 5,735,887 A | 4/1998 | Barreras et al. |
| 5,762,599 A | 6/1998 | Sohn |
| 5,782,774 A | 7/1998 | Shmulewitz |
| 5,800,464 A | 9/1998 | Kieval et al. |
| 5,800,502 A | 9/1998 | Boutos |
| 5,814,089 A | 9/1998 | Stokes et al. |
| 5,873,865 A | 2/1999 | Horzewski et al. |
| 5,900,433 A | 5/1999 | Igo et al. |
| 5,902,712 A | 5/1999 | Axelgaard |
| 5,904,711 A | 5/1999 | Flom et al. |
| 5,904,712 A | 5/1999 | Axelgaard |
| 5,906,641 A | 5/1999 | Thompson |
| 5,913,876 A | 6/1999 | Taylor |
| 5,916,239 A | 6/1999 | Geddes et al. |
| 5,925,061 A | 7/1999 | Ogi et al. |
| 5,935,077 A | 8/1999 | Ogle |
| 5,948,006 A | 9/1999 | Mann |
| 5,967,986 A | 10/1999 | Cimochowski et al. |
| 5,994,444 A | 11/1999 | Trescony et al. |
| 5,997,563 A | 12/1999 | Kretzers |
| 6,014,589 A | 1/2000 | Farley et al. |
| 6,023,640 A | 2/2000 | Ross |
| 6,029,091 A | 2/2000 | De La Rama et al. |
| 6,038,485 A | 3/2000 | Axelgaard |
| 6,053,873 A | 4/2000 | Govari |
| 6,058,331 A | 5/2000 | King |
| 6,073,048 A | 6/2000 | Kieval et al. |
| 6,086,527 A | 7/2000 | Talpade |
| 6,104,956 A | 8/2000 | Naritoku et al. |
| 6,106,477 A | 8/2000 | Miesel et al. |
| 6,120,520 A | 9/2000 | Saadat |
| 6,141,587 A | 10/2000 | Mower et al. |
| 6,178,349 B1 | 1/2001 | Kieval |
| 6,200,259 B1 | 3/2001 | March |
| 6,201,991 B1 | 3/2001 | Chekanov |
| 6,231,516 B1 | 5/2001 | Keilman et al. |
| 6,245,103 B1 | 6/2001 | Stinson |
| 6,246,911 B1 | 6/2001 | Seligman |
| 6,270,524 B1 | 8/2001 | Kim |
| 6,273,910 B1 | 8/2001 | Limon |
| 6,277,078 B1 | 8/2001 | Porat et al. |
| 6,280,377 B1 | 8/2001 | Talpade |
| 6,292,695 B1 | 9/2001 | Webster et al. |
| 6,317,631 B1 | 11/2001 | Ben-Haim et al. |
| 6,339,725 B1 | 1/2002 | Naritoku et al. |
| 6,347,247 B1 | 2/2002 | Dev |
| 6,411,845 B1 | 6/2002 | Mower et al. |
| 6,418,348 B1 | 7/2002 | Witte |
| 6,423,084 B1 | 7/2002 | Germain |
| 6,440,059 B1 | 8/2002 | Haas et al. |
| 6,445,953 B1 | 9/2002 | Bulkes |
| 6,463,323 B1 | 10/2002 | Conrad-Vlasak |
| 6,473,644 B1 | 10/2002 | Terry et al. |
| 6,480,747 B2 | 11/2002 | Schmidt |
| 6,485,524 B2 | 11/2002 | Strecker |
| 6,496,732 B1 | 12/2002 | Wallace |
| 6,522,926 B1 | 2/2003 | Kieval et al. |
| 6,532,388 B1 | 3/2003 | Hill et al. |
| 6,575,994 B1 | 6/2003 | Marin et al. |
| 6,582,461 B1 | 6/2003 | Burmeister et al. |
| 6,611,715 B1 | 8/2003 | Boveja |
| 6,615,085 B1 | 9/2003 | Boveja |
| 6,616,613 B1 | 9/2003 | Goodma et al. |
| 6,616,624 B1 | 9/2003 | Kieval |
| 6,622,041 B2 | 9/2003 | Terry, Jr. et al. |
| 6,631,296 B1 | 10/2003 | Parramon et al. |
| 6,632,991 B2 | 10/2003 | Chen |
| 6,647,287 B1 | 11/2003 | Peel, III |
| 6,656,960 B2 | 12/2003 | Puskas |
| 6,668,191 B1 | 12/2003 | Boveja |
| 6,682,480 B1 | 1/2004 | Habib et al. |
| 6,721,603 B2 | 4/2004 | Zabara et al. |
| 6,810,286 B2 | 10/2004 | Donovan |
| 6,824,561 B2 | 11/2004 | Soykan |
| 6,845,267 B2 | 1/2005 | Harrison |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst |
| 6,934,583 B2 | 8/2005 | Weinberg et al. |
| 6,939,345 B2 | 9/2005 | KenKnight |
| 6,947,792 B2 | 9/2005 | Ben-Haim et al. |
| 6,957,107 B2 | 10/2005 | Rogers et al. |
| 6,985,774 B2 | 1/2006 | Kieval et al. |
| 7,044,981 B2 | 5/2006 | Liu et al. |
| 7,062,318 B2 | 6/2006 | Ben-Haim et al. |
| 7,076,307 B2 | 7/2006 | Boveja et al. |
| 7,079,901 B1 | 7/2006 | Loftin et al. |
| 7,082,336 B2 | 7/2006 | Ransbury et al. |
| 7,090,648 B2 | 8/2006 | Sackner et al. |
| 7,123,961 B1 | 10/2006 | Kroll et al. |
| 7,149,574 B2 | 12/2006 | Yun et al. |
| 7,158,832 B2 | 1/2007 | Kieval et al. |
| 7,167,751 B1 | 1/2007 | Whitehurst et al. |
| 7,191,007 B2 | 3/2007 | Desai et al. |
| 7,191,012 B2 | 3/2007 | Boveja et al. |
| 7,201,719 B2 | 4/2007 | Feliss et al. |
| 7,206,637 B2 | 4/2007 | Salo |
| 7,225,019 B2 | 5/2007 | Jahns et al. |
| 7,228,167 B2 | 6/2007 | Kara et al. |
| 7,229,403 B2 | 6/2007 | Schock |
| 7,263,405 B2 | 8/2007 | Boveja et al. |
| 7,269,457 B2 | 9/2007 | Shafer et al. |
| 7,277,761 B2 | 10/2007 | Shelchuk |
| 7,291,113 B2 | 11/2007 | Satoh |
| 7,292,886 B1 | 11/2007 | Kroll |
| 7,299,091 B2 | 11/2007 | Barrett et al. |
| 7,321,793 B2 | 1/2008 | Ben Ezra et al. |
| 7,363,076 B2 | 4/2008 | Yun et al. |
| 7,367,970 B2 | 5/2008 | Govari et al. |
| 7,389,149 B2 | 6/2008 | Rossing et al. |
| 7,395,119 B2 | 7/2008 | Hagen et al. |
| 7,444,183 B2 | 10/2008 | Knudson et al. |
| 7,452,334 B2 | 11/2008 | Gianchandani |

(56) References Cited

U.S. PATENT DOCUMENTS

| | | |
|---|---|---|
| 7,471,986 B2 | 12/2008 | Hatlestad |
| 7,476,200 B2 | 1/2009 | Tal |
| 7,480,532 B2 | 1/2009 | Kieval et al. |
| 7,486,991 B2 | 2/2009 | Libbus et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,519,421 B2 | 4/2009 | Denker et al. |
| 7,555,344 B2 | 6/2009 | Maschino et al. |
| 7,561,918 B2 | 7/2009 | Armstrong et al. |
| 7,570,999 B2 | 8/2009 | Libbus et al. |
| 7,613,511 B2 | 11/2009 | Wu et al. |
| 7,613,515 B2 | 11/2009 | Knudson et al. |
| 7,616,997 B2 | 11/2009 | Kieval et al. |
| 7,617,003 B2 | 11/2009 | Caparso et al. |
| 7,623,926 B2 | 11/2009 | Rossing et al. |
| 7,634,315 B2 | 12/2009 | Cholette |
| 7,706,875 B2 | 4/2010 | Buras et al. |
| 7,706,884 B2 | 4/2010 | Libbus |
| 7,706,886 B2 | 4/2010 | Morimoto et al. |
| 7,715,915 B1 | 5/2010 | Ryu et al. |
| 7,720,547 B2 | 5/2010 | Denker et al. |
| 7,725,194 B2 | 5/2010 | Klostermann et al. |
| 7,738,961 B2 | 6/2010 | Sharma |
| 7,747,302 B2 | 6/2010 | Milledge |
| 7,765,000 B2 | 7/2010 | Zhang et al. |
| 7,765,008 B2 | 7/2010 | Ben-Haim et al. |
| 7,769,446 B2 | 8/2010 | Moffitt et al. |
| 7,780,719 B2 | 8/2010 | Killion et al. |
| 7,801,604 B2 | 9/2010 | Brockway et al. |
| 7,811,221 B2 | 10/2010 | Gross |
| 7,813,805 B1 | 10/2010 | Farazi |
| 7,813,812 B2 | 10/2010 | Kieval et al. |
| 7,826,899 B1 | 11/2010 | Ryu et al. |
| 7,840,282 B2 | 11/2010 | Williams et al. |
| 7,848,820 B2 | 12/2010 | Abrahamson |
| 7,856,273 B2 | 12/2010 | Maschino et al. |
| 7,860,566 B2 | 12/2010 | Mazgalev et al. |
| 7,869,870 B1 | 1/2011 | Farazi |
| 7,881,782 B2 | 2/2011 | Libbus et al. |
| 7,881,792 B1 | 2/2011 | Farazi |
| 7,894,902 B2 | 2/2011 | Rom |
| 7,899,554 B2 | 3/2011 | Williams et al. |
| 7,949,400 B2 | 5/2011 | Kieval et al. |
| 7,991,474 B2 | 8/2011 | Aldrich et al. |
| 8,046,085 B2 | 10/2011 | Knudson et al. |
| 8,065,019 B2 | 11/2011 | Marnfeldt et al. |
| 8,086,314 B1 | 12/2011 | Kieval |
| 8,095,218 B2 | 1/2012 | Gross et al. |
| 8,121,692 B2 | 2/2012 | Haefner et al. |
| 8,131,362 B2 | 3/2012 | Moffitt et al. |
| 8,150,508 B2 | 4/2012 | Craig |
| 8,160,701 B2 | 4/2012 | Zhao et al. |
| 8,175,705 B2 | 5/2012 | Libbus |
| 8,224,437 B2 | 7/2012 | Kieval et al. |
| 8,244,378 B2 | 8/2012 | Bly et al. |
| 8,249,705 B1 | 8/2012 | Kieval |
| 8,290,595 B2 | 10/2012 | Kieval et al. |
| 8,386,038 B2 | 2/2013 | Bianchi et al. |
| 8,391,970 B2 | 3/2013 | Tracey et al. |
| 8,406,868 B2 | 3/2013 | Buschman et al. |
| 8,442,639 B2 | 5/2013 | Walker et al. |
| 8,449,472 B2 | 5/2013 | Ryu et al. |
| 8,457,743 B2 | 6/2013 | Gollasch et al. |
| 8,457,748 B2 | 6/2013 | Lange |
| 8,463,392 B2 | 6/2013 | Aghassian |
| 8,467,884 B2 | 6/2013 | Chen et al. |
| 8,478,414 B2 | 7/2013 | Kieval et al. |
| 8,498,704 B2 | 7/2013 | Shuros et al. |
| 8,504,161 B1 | 8/2013 | Kornet et al. |
| 8,509,919 B2 | 8/2013 | Yoo et al. |
| 8,521,293 B2 | 8/2013 | Anderson et al. |
| 8,538,535 B2 | 9/2013 | Gross |
| 8,538,542 B2 | 9/2013 | Knudson et al. |
| 8,560,076 B2 | 10/2013 | Kieval et al. |
| 8,571,654 B2 | 10/2013 | Libbus et al. |
| 8,571,664 B2 | 10/2013 | Anderson et al. |
| 8,577,458 B1 | 11/2013 | Libbus et al. |
| 8,600,505 B2 | 12/2013 | Libbus et al. |
| 8,600,511 B2 | 12/2013 | Yared et al. |
| 8,600,521 B2 | 12/2013 | Armstrong et al. |
| 8,606,359 B2 | 12/2013 | Rossing et al. |
| 8,612,014 B2 | 12/2013 | Rahman et al. |
| 8,620,422 B2 | 12/2013 | Kieval et al. |
| 8,620,450 B2 | 12/2013 | Tockman et al. |
| 8,626,290 B2 | 1/2014 | Dagan |
| 8,626,299 B2 | 1/2014 | Gross et al. |
| 8,630,709 B2 | 1/2014 | Libbus et al. |
| 8,634,928 B1 | 1/2014 | ODriscoll et al. |
| 8,639,327 B2 | 1/2014 | Zhou et al. |
| 8,639,339 B2 | 1/2014 | Bange et al. |
| 8,644,928 B2 | 2/2014 | Takata |
| 8,660,666 B2 | 2/2014 | Craig |
| 8,663,103 B2 | 3/2014 | Causey et al. |
| 8,670,835 B2 | 3/2014 | Park et al. |
| 8,700,145 B2 | 4/2014 | Kilgard et al. |
| 8,700,157 B2 | 4/2014 | Goetz et al. |
| 8,700,173 B2 | 4/2014 | Edlund |
| 8,706,223 B2 | 4/2014 | Zhou et al. |
| 8,712,531 B2 | 4/2014 | Kieval et al. |
| 8,729,129 B2 | 5/2014 | Tracey et al. |
| 8,731,663 B2 | 5/2014 | Bianchi et al. |
| 8,738,126 B2 | 5/2014 | Craig |
| 8,744,586 B2 | 6/2014 | Georgakopoulos et al. |
| 8,755,907 B2 | 6/2014 | Kieval et al. |
| 8,788,028 B2 | 7/2014 | Kumar et al. |
| 8,788,066 B2 | 7/2014 | Cates et al. |
| 8,805,513 B2 | 8/2014 | Libbus |
| 8,818,508 B2 | 8/2014 | Scheiner |
| 8,818,524 B2 | 8/2014 | Hincapie et al. |
| 8,880,185 B2 | 11/2014 | Hastings et al. |
| 8,929,990 B2 | 1/2015 | Moffitt et al. |
| 2001/0044434 A1 | 11/2001 | Lee et al. |
| 2002/0016615 A1 | 2/2002 | Dev |
| 2002/0026228 A1 | 2/2002 | Schauerte |
| 2002/0032468 A1 | 3/2002 | Hill |
| 2002/0055764 A1* | 5/2002 | Malonek ............... A61N 1/05 607/122 |
| 2002/0077554 A1 | 6/2002 | Schwartz |
| 2002/0103454 A1 | 8/2002 | Sackner |
| 2002/0161377 A1 | 10/2002 | Rabkin |
| 2002/0169413 A1 | 11/2002 | Keren |
| 2002/0198571 A1 | 12/2002 | Puskas |
| 2003/0036773 A1 | 2/2003 | Whitehurst |
| 2003/0050683 A1 | 3/2003 | Boutos |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0060858 A1 | 3/2003 | Kieval et al. |
| 2003/0109914 A1 | 6/2003 | Westlund et al. |
| 2003/0130715 A1 | 7/2003 | Boutos |
| 2003/0199806 A1 | 10/2003 | Kieval |
| 2003/0204206 A1 | 10/2003 | Padua |
| 2004/0010303 A1 | 1/2004 | Bolea et al. |
| 2004/0019364 A1 | 1/2004 | Kieval |
| 2004/0039417 A1 | 2/2004 | Soykan |
| 2004/0044393 A1 | 3/2004 | Yarden |
| 2004/0054384 A1 | 3/2004 | Nachum |
| 2004/0064090 A1 | 4/2004 | Keren |
| 2004/0082948 A1 | 4/2004 | Stewart et al. |
| 2004/0106954 A1 | 6/2004 | Whitehurst et al. |
| 2004/0106976 A1 | 6/2004 | Bailey et al. |
| 2004/0133240 A1 | 7/2004 | Adams |
| 2004/0162590 A1 | 8/2004 | Whitehurst et al. |
| 2004/0193092 A1 | 9/2004 | Deal |
| 2004/0199210 A1 | 10/2004 | Shelchuk |
| 2004/0210261 A1 | 10/2004 | King et al. |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0049680 A1 | 3/2005 | Fischell et al. |
| 2005/0065553 A1 | 3/2005 | Ben Ezra et al. |
| 2005/0090867 A1 | 4/2005 | Lapanashvili |
| 2005/0096710 A1 | 5/2005 | Kieval et al. |

(56) References Cited

U.S. PATENT DOCUMENTS

| | | |
|---|---|---|
| 2005/0143785 A1 | 6/2005 | Libbus |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0203610 A1 | 9/2005 | Tzeng |
| 2005/0209652 A1 | 9/2005 | Whitehurst et al. |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2005/0283184 A1 | 12/2005 | Gilson et al. |
| 2005/0288651 A1 | 12/2005 | Van Tassel et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0276844 A1 | 12/2006 | Alon |
| 2006/0287705 A1 | 12/2006 | Weber |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0100433 A1 | 5/2007 | Limon |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | Karashurov |
| 2007/0156198 A1 | 7/2007 | Rossing et al. |
| 2007/0156201 A1 | 7/2007 | Rossing |
| 2007/0167984 A1 | 7/2007 | Kieval et al. |
| 2007/0185540 A1 | 8/2007 | Ben Haim et al. |
| 2007/0185542 A1 | 8/2007 | Bolea et al. |
| 2007/0185543 A1 | 8/2007 | Rossing et al. |
| 2007/0191904 A1 | 8/2007 | Libbus et al. |
| 2007/0196428 A1 | 8/2007 | Glauser et al. |
| 2007/0198064 A1 | 8/2007 | Lapanashvili et al. |
| 2007/0815543 | 8/2007 | Rossing et al. |
| 2007/0248676 A1 | 10/2007 | Stamler et al. |
| 2007/0248850 A1 | 10/2007 | Heller |
| 2007/0255379 A1 | 11/2007 | Williams et al. |
| 2007/0276270 A1 | 11/2007 | Tran |
| 2007/0276442 A1 | 11/2007 | Hagen et al. |
| 2007/0276459 A1 | 11/2007 | Rossing et al. |
| 2007/0282385 A1 | 12/2007 | Rossing et al. |
| 2007/0288076 A1 | 12/2007 | Bulkes et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0046016 A1 | 2/2008 | Ben-David |
| 2008/0046054 A1 | 2/2008 | Hjelle et al. |
| 2008/0051767 A1 | 2/2008 | Rossing et al. |
| 2008/0051849 A1 | 2/2008 | Ben Haim et al. |
| 2008/0058872 A1 | 3/2008 | Brockway et al. |
| 2008/0058889 A1 | 3/2008 | Ben Haim et al. |
| 2008/0058891 A1 | 3/2008 | Ben Haim et al. |
| 2008/0071363 A1 | 3/2008 | Tuval et al. |
| 2008/0082137 A1 | 4/2008 | Kieval et al. |
| 2008/0097540 A1 | 4/2008 | Bolea et al. |
| 2008/0119898 A1 | 5/2008 | Ben-David |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0154349 A1 | 6/2008 | Rossing et al. |
| 2008/0161865 A1 | 7/2008 | Hagen |
| 2008/0161887 A1 | 7/2008 | Hagen |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0183254 A1 | 7/2008 | Bly et al. |
| 2008/0194996 A1* | 8/2008 | Kassab .................. 600/593 |
| 2008/0195174 A1 | 8/2008 | Walker et al. |
| 2008/0215117 A1 | 9/2008 | Gross |
| 2009/0005859 A1 | 1/2009 | Keilman |
| 2009/0036975 A1 | 2/2009 | Ward |
| 2009/0062874 A1 | 3/2009 | Teacey et al. |
| 2009/0112285 A1 | 4/2009 | Cahan et al. |
| 2009/0171425 A1 | 7/2009 | Dahlberg |
| 2009/0198097 A1 | 8/2009 | Gross |
| 2009/0198308 A1* | 8/2009 | Gross .................. A61N 1/05 607/72 |
| 2009/0204170 A1 | 8/2009 | Hastings |
| 2009/0228078 A1 | 9/2009 | Zhang et al. |
| 2010/0004650 A1 | 1/2010 | Ormsby et al. |
| 2010/0010556 A1 | 1/2010 | Zhao et al. |
| 2010/0042186 A1 | 2/2010 | Ben-David et al. |
| 2010/0076247 A1 | 3/2010 | Zilbershlag et al. |
| 2010/0094373 A1 | 4/2010 | Sharma |
| 2010/0211131 A1 | 8/2010 | Williams et al. |
| 2010/0280568 A1 | 11/2010 | Bulkes et al. |
| 2010/0280593 A1 | 11/2010 | Richter |
| 2010/0305392 A1 | 12/2010 | Gross et al. |
| 2011/0106237 A1 | 5/2011 | Bonsignore et al. |
| 2011/0118773 A1 | 5/2011 | Gross et al. |
| 2011/0137370 A1 | 6/2011 | Gross |
| 2012/0035679 A1 | 2/2012 | Dagan et al. |
| 2012/0035711 A1 | 2/2012 | Gross et al. |
| 2012/0158081 A1 | 6/2012 | Gross et al. |
| 2012/0303112 A1 | 11/2012 | Armstrong et al. |
| 2013/0123880 A1 | 5/2013 | Dagan |

FOREIGN PATENT DOCUMENTS

| | | |
|---|---|---|
| WO | 99/26530 | 6/1999 |
| WO | WO 00/02501 | 1/2000 |
| WO | WO 02/26314 | 4/2002 |
| WO | WO 03/076008 | 9/2003 |
| WO | WO 03/082080 | 10/2003 |
| WO | WO 03/082403 | 10/2003 |
| WO | WO 2004/073484 | 9/2004 |
| WO | 2005/065771 A1 | 7/2005 |
| WO | WO 2005/084389 | 9/2005 |
| WO | WO 2005/097256 | 10/2005 |
| WO | WO 2006/012033 | 2/2006 |
| WO | WO 2006/012050 | 2/2006 |
| WO | WO 2006/032902 | 3/2006 |
| WO | WO 2006/041664 | 4/2006 |
| WO | WO 2006/064503 | 6/2006 |
| WO | 2006/098928 | 9/2006 |
| WO | WO 2006/094273 | 9/2006 |
| WO | WO 2006/123346 | 11/2006 |

(56) References Cited

FOREIGN PATENT DOCUMENTS

| WO | WO 2006/125163 | 11/2006 |
|---|---|---|
| WO | WO 2007/013065 | 2/2007 |
| WO | WO 2007/047152 | 4/2007 |
| WO | WO 2007/064895 | 6/2007 |
| WO | WO 2007/106533 | 9/2007 |
| WO | WO 2007/113818 | 10/2007 |
| WO | WO 2007/113833 | 10/2007 |
| WO | WO 2007/114860 | 10/2007 |
| WO | WO 2007/118090 | 10/2007 |
| WO | WO 2007/136850 | 11/2007 |
| WO | WO 2007/136851 | 11/2007 |
| WO | WO 2008/039982 | 4/2008 |
| WO | WO 2008/083120 | 7/2008 |
| WO | WO 2008/083235 | 7/2008 |
| WO | WO 2008/100390 | 8/2008 |
| WO | 2009/017647 | 2/2009 |
| WO | WO 2009/095918 | 8/2009 |
| WO | WO 2009/095920 | 8/2009 |
| WO | 2012017437 A1 | 2/2012 |
| WO | 2012/085907 A2 | 6/2012 |
| WO | 2013/035092 A2 | 3/2013 |
| WO | 2013/069020 A1 | 5/2013 |
| WO | 2013/164829 A1 | 11/2013 |

OTHER PUBLICATIONS

An Office Action dated Sep. 18, 2012, which issued during the prosecution of U.S. Appl. No. 12/023,896.
An English Translation of an Office Action dated Oct. 8, 2012, which issued during the prosecution of Chinese Patent Application No. 200980111617.8.
An Office Action dated Jun. 19, 2012, which issued during the prosecution of U.S. Appl. No. 11/995,904.
An Office Action dated Jul. 18, 2012, which issued during the prosecution of U.S. Appl. No. 13/210,778.
An Office Action dated Aug. 29, 2012, which issued during the prosecution of U.S. Appl. No. 12/792,227.
An Office Action dated Aug. 1, 2012, which issued during the prosecution of U.S. Appl. No. 12/957,799.
An International Search Report and a Written Opinion both dated Jul. 5, 2012, which issued during the prosecution of Applicant's PCT/IL11/00952.
The unequal influences of the left and right vagi on the control of the heart and pulmonary artery in the rattlesnake, Crotalus durissus, by Taylor, The Journal of Experimental Biology 212, 145-151 Aug. 2008.
Coronary vascular sympathetic beta-receptor innervation, by Hamiton, American Journal of Physiology, vol. 230, No. 6, Jun. 1976.
An Office Action dated Aug. 9, 2011, which issued during the prosecution of U.S. Appl. No. 12/023,896.
An International Search Report and a Written Opinion both dated Aug. 8, 2013, which issued during the prosecution of Applicant's PCT/IL2013/050375.
An Office Action dated Dec. 13, 2013, which issued during the prosecution of U.S. Appl. No. 13/294,062.
An Office Action dated Jan. 27, 2014, which issued during the prosecution of U.S. Appl. No. 12/023,896.
An Office Action dated Nov. 12, 2013, which issued during the prosecution of U.S. Appl. No. 11/995,904.
An International Search Report and a Written Opinion both dated Dec. 19, 2011, which issued during the prosecution of Applicant's PCT/IL11/00636.
An Office Action dated Mar. 13, 2012, which issued during the prosecution of U.S. Appl. No. 12/023,896.
An Office Action dated Mar. 15, 2012, which issued during the prosecution of U.S. Appl. No. 12/792,227.
A Supplementary European search Report dated Dec. 14, 2012, which issued during the prosecution of European Patent Application No. 06766171.

Restriction Requirement dated Jun. 7, 2012 issued during the prosecution of U.S. Appl. No. 12/851,214.
An Office Action dated Oct. 2, 2012, which issued during the prosecution of U.S. Appl. No. 12/851,214.
Sherman AJ, "Blockade of nitric oxide synthesis reduces myocardial oxygen consumption in vivo", Circulation 95:1328-1334, 1997.
Kugiyama K, "Nitric oxide activity is deficient in spasm arteries of patients with coronary spastic angina", Circulation 94:266-272, 1996.
Sabbah H et al., "Global left ventricular remodeling with the Acorn Cardiac Support Device: Hemodynamic and angiographic findings in dogs with heart failure", Heart Failure 10(2): 109-115, 2005. (Only First Page).
"Improving the Thromboresistivity of Chemical Sensors via Nitric Oxide Release: Fabrication and in Vivo Evaluation of NO-Releasing Oxygen-Sensing Catheters," by MH Schoenfisch et al., Anal. Chem., 72 (6), 1119-1126, 2000.
"Endogenous and Exogenous Nitric Oxide Protect Against Intracoronary Thrombosis and Reocclusion After Thrombolysis," by Sheng-Kun Yao et al., Circulation. 1995;92: 1005-1010.
"Improving the biocompatibility of in vivo sensors via nitric oxide release," by Jae Ho Shin et al., Analyst, 2006, 131, 609-615.
Cheetah Medical Inc. manufactures the Cheetah Reliant, Jan. 23, 2008.
CardioMEMS, Inc., manufactures the EndoSure® Wireless AAA Pressure Measurement System, Nov. 11, 2005.
Sulzer IntraTherapeutics Inc. manufactures the IntraCoil® Self-Expanding Peripheral Stent (IntraCoil® Stent), Jun. 28, 2002.
"Comparison of neurogenic contraction and relaxation in canine corpus cavernosum and penile artery and vein", Hayashida, et al. Jpn. J. Pharmacol. 72:231-240 (1996), p. 232 col. 2, para 1; p. 238, col. 2, para 2.
An International Search Report and a Written Opinion both dated Jul. 13, 2009, which issued during the prosecution of Applicant's PCT/IL09/00117.
An International Search Report and a Written Opinion both dated May 12, 2009, which issued during the prosecution of Applicant's PCT/IL09/00115.
An Office Action dated Nov. 18, 2009, which issued during the prosecution of Applicant's U.S. Appl. No. 12/023,900.
"Vagus nerve stimulation as a method to temporarily slow or arrest the heart," by Matheny, Ann Thorac Surg. Jun. 1997;63(6 Suppl):S28-9—an abstract.
"Heart rate variability," by Task Force of the European Society of Cardiology and the North American Society of Pacing and Electrophysiology, European Heart Journal (1996) 17, 354-381.
"Heart rate and vasomotor control during exercise," by Vallais, Proceedings of the 29th Annual International Conference of the IEEE EMBS, Cité Internationale, Lyon, France, Aug. 23-26, 2007.
"Effects of chronic baroreceptor stimulation on the autonomic cardiovascular regulation in patients with drug-resistant arterial hypertension," by Wustmann, Hypertension 2009;54;530-536.
Biosense Webster, Inc. (CA, USA) manufactures the LASSO 2515 Variable Circular Mapping Catheter.
"Sympathovagal balance is major determinant of short-term blood pressure variability in healthy subjects," by Laitinen, Am J Physiol Heart Circ Physiol 276:1245-1252, 1999.
"Optimal frequency ranges for extracting information on cardiovascular autonomic control from the blood pressure and pulse interval spectrograms in mice," by Baudrie, Am J Physiol Regul Integr Comp Physiol 292: R904-R912, 2007.
"Neural influences on cardiovascular variability: possibilities and pitfalls," by Malpas, Am J Physiol Heart Circ Physiol 282: H6-H20, 2002.
"Vagus nerve stimulation decreases left ventricular contractility in vivo in the human and pig heart," by Lewis, J Physiol. Jul. 15, 2001; 534(Pt 2): 547-552.
An International Preliminary Examination Report on Patentability dated Aug. 12, 2010, which issued during the prosecution of Applicant's PCT/IL09/00117.
An International Preliminary Examination Report on Patentability dated Aug. 12, 2010, which issued during the prosecution of Applicant's PCT/IL09/00115.

(56) References Cited

OTHER PUBLICATIONS

Mc Frost, et al., "Preparation and characterization of implantable sensors with nitric oxide release coating", Microchemical Journal vol. 74 Issue: 3 Jun. 2003, pp. 277-288.
Paulus WJ, "Beneficial effects of nitric oxide on cardiac diastolic function: the flip side of the coin", Heart Failure Review 5(4): 337-344 (2000).
Gong Z, "Loss of nitric oxide production in the coronary circulation after the development of dilated cardiomyopathy: a specific defect in the neural regulation of coronary blood flow", Clinical and Experimental Pharmacology and Physiology 23(8): 715-721 (1996).
An Office Action dated Nov. 7, 2014, which issued during the prosecution of U.S. Appl. No. 13/741,154.
European Search Report dated Jul. 30, 2014, which issued during the prosecution of Applicant's European App No. 11814203.3.
An Office Action dated Jan. 5, 2015, which issued during the prosecution of U.S. Appl. No. 12/959,126.
An Office Action dated Jan. 15, 2015, which issued during the prosecution of U.S. Appl. No. 14/356,829.
An International Search Report and a Written Opinion both dated Apr. 16, 2015, which issued during the prosecution of Applicant's PCT/IL2014/050972.
An Office Action dated Sep. 15, 2015, which issued during the prosecution of U.S. Appl. No. 14/356,829.
An Office Action dated Sep. 28, 2015, which issued during the prosecution of U.S. Appl. No. 14/144,024.
An Office Action dated Jan. 4, 2016, which issued during the prosecution of U.S. Appl. No. 13/741,154.
An Office Action dated May 22, 2015, which issued during the prosecution of U.S. Appl. No. 13/741,154.

* cited by examiner

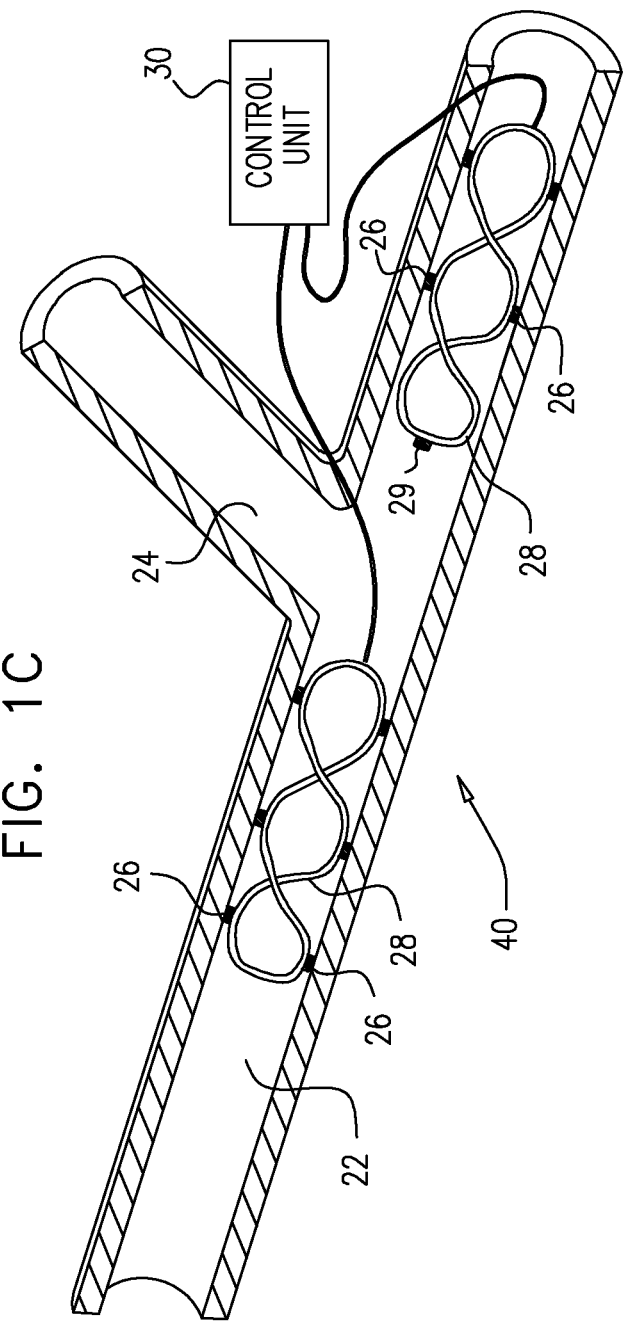

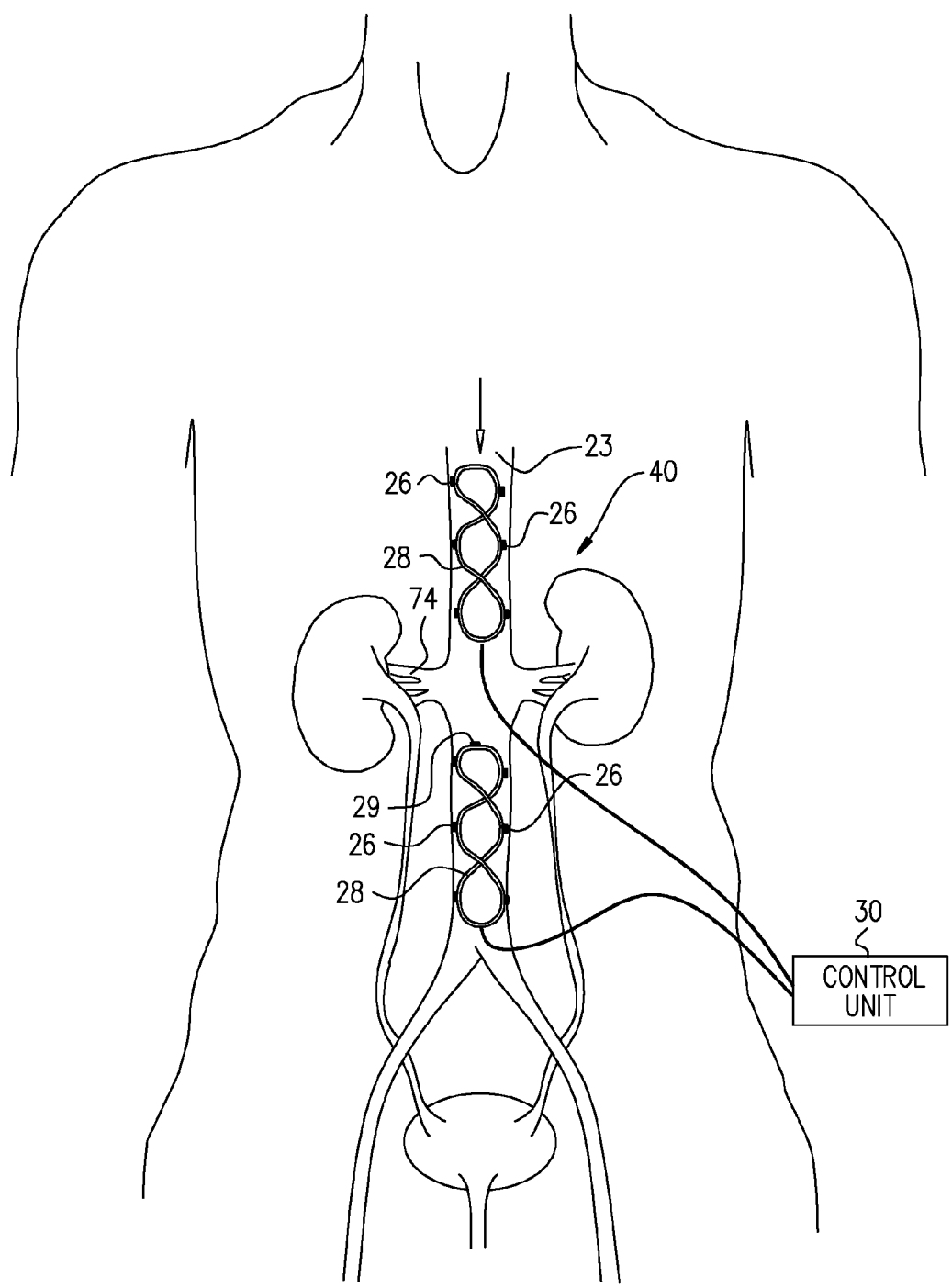

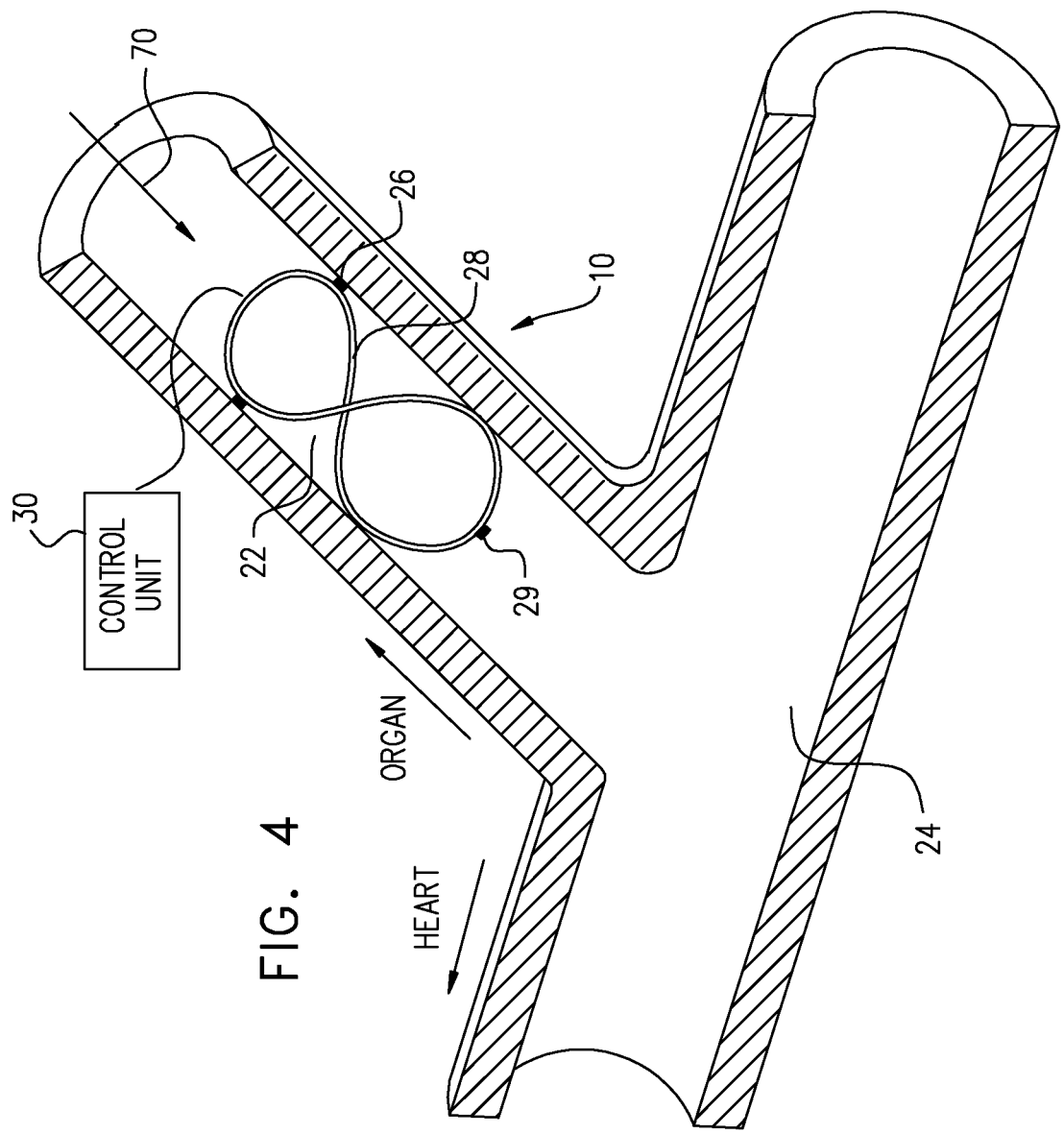

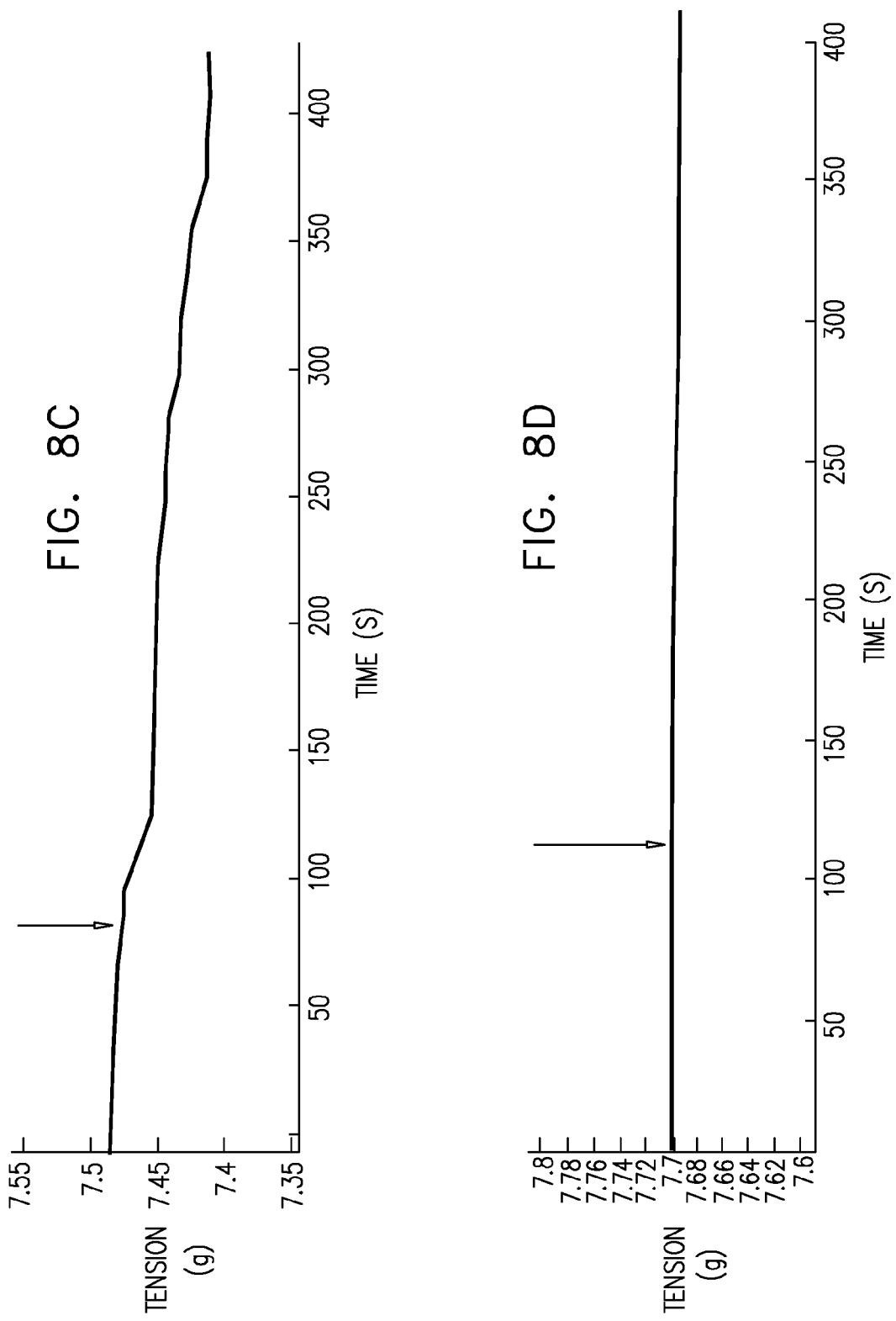

ENHANCING PERFUSION BY CONTRACTION

CROSS REFERENCES TO RELATED APPLICATIONS

The present application is a continuation of U.S. application Ser. No. 12/851,214 (issued as U.S. Pat. No. 8,538,535) to Gross, filed Aug. 5, 2010, entitled, "Enhancing perfusion by contraction," which is incorporated herein by reference.

FIELD OF EMBODIMENTS OF THE INVENTION

Some applications of the present invention generally relate to medical apparatus. Specifically, some applications of the present invention relate to an electrode device for enhancing perfusion to blood vessels.

BACKGROUND

Renal artery stenosis is the narrowing of the renal artery, often caused by atherosclerosis or fibromuscular dysplasia. This narrowing of the renal artery can impede blood flow to the kidneys, resulting in poor perfusion of the kidneys, reduced kidney function, and possible renal failure.

A stroke is the clinical designation for a rapidly developing loss of brain function due to a disturbance in the blood vessels supplying blood to the brain. This phenomenon can be due to ischemia (lack of blood supply) caused by thrombosis or embolism, or due to a hemorrhage, highlighting the desirability for increasing the cerebral perfusion of a patient.

US 2009/0198308 to Gross describes apparatus including a sensing electrode configured to be implanted at a non-cardiac site in a vicinity of an aorta of a subject and to detect an electrical parameter of the aorta, and a control unit configured to receive the detected parameter and to generate an output in response to the detected parameter. Additional embodiments are also described.

US 2009/0198097 to Gross describes apparatus for treating erectile dysfunction of a subject. The apparatus includes one or more electrodes configured to be coupled to a vicinity of a blood vessel that carries blood into or out of a penis of the subject, and a control unit configured to facilitate erection of the penis by peristaltically pumping blood in the blood vessel by stimulating nitric oxide (NO) production in the vicinity, by driving the electrodes to drive a current into the vicinity. Additional embodiments are also described.

PCT Publication WO 07/013,065 to Gross describes a bifurcation stent comprising one or more electrodes, the stent configured to be placed in a primary passage and a secondary passage of a blood vessel, and a control unit, configured to drive the electrodes to apply a signal to a wall of the blood vessel, and to configure the signal to increase nitric oxide (NO) secretion by the wall.

U.S. Pat. No. 6,616,624 to Kieval describes devices, systems and methods by which the real or apparent renovascular perfusion and intrarenal pressure may be selectively and controllably increased. The Kieval patent states that by selectively and controllably increasing renovascular perfusion and interstitial hydrostatic pressure when the heart is unable to pump sufficient blood or when renal perfusion is suboptimal, neurohormonal activation and fluid retention is reduced or reversed, thereby minimizing their deleterious effects on the heart, vasculature, kidneys and other body systems.

US Patent Application Publication 2004/0054384 to Nachum et al. describes a treatment method and device for promoting a localized increase in the flow of blood through a blood vessel in an area of the body, the method including the steps of: (a) providing a system including: (i) at least a first electrode operatively contacting a first portion of body tissue; (ii) at least a second electrode operatively contacting a second portion of body tissue; and (iii) a signal generator, operatively connected to the first electrode and the second electrode, for providing a plurality of electrical impulses to the electrodes; (b) applying the electrical impulses so as to subject the muscular tissue to at least one voltage differential, thereby inducing repeated, contracting, directional movement of muscular tissue associated within the blood vessel, so as to produce a localized increase in the flow of blood through the blood vessel.

The following references may be of interest:
U.S. Pat. No. 4,809,676 to Freeman
U.S. Pat. No. 5,324,323 to Bui
U.S. Pat. No. 5,372,573 to Habib
U.S. Pat. No. 5,612,314 to Stamler
U.S. Pat. No. 5,669,924 to Shaknovich
U.S. Pat. No. 5,782,774 to Shmulewitz
U.S. Pat. No. 5,900,433 to Igo
U.S. Pat. No. 5,904,712 to Axelgaard
U.S. Pat. No. 5,906,641 to Thompson
U.S. Pat. No. 5,913,876 to Taylor
U.S. Pat. No. 5,935,077 to Ogle
U.S. Pat. No. 6,038,485 to Axelgaard
U.S. Pat. No. 6,058,331 to King
U.S. Pat. No. 6,086,527 to Talpade
U.S. Pat. No. 6,106,477 to Miesel
U.S. Pat. No. 6,200,259 to March
U.S. Pat. No. 6,245,103 to Stinson
U.S. Pat. No. 6,280,377 to Talpade
U.S. Pat. No. 6,347,247 to Dev
U.S. Pat. No. 6,463,323 to Conrad-Vlasak
U.S. Pat. No. 6,485,524 to Strecker
U.S. Pat. No. 6,721,603 to Zabara
U.S. Pat. No. 6,810,286 to Donovan
U.S. Pat. No. 6,824,561 to Soykan
U.S. Pat. No. 6,845,267 to Harrison
U.S. Pat. No. 6,865,416 to Dev
U.S. Pat. No. 6,871,092 to Piccone
U.S. Pat. No. 6,939,345 to KenKnight
U.S. Pat. No. 7,082,336 to Ransbury
U.S. Pat. No. 7,090,648 to Sackner
U.S. Pat. No. 7,167,751 to Whitehurst
U.S. Pat. No. 7,206,637 to Salo
U.S. Pat. No. 7,229,403 to Schock
U.S. Pat. No. 7,269,457 to Shafer
US 2002/0169413 to Keren
US 2002/0103454 to Sackner
US 2003/0036773 to Whitehurst
US 2003/0204206 to Padua
US 2004/0039417 to Soykan
US 2004/0064090 to Keren
US 2004/0106954 to Whitehurst
US 2005/0154418 to Kieval
US 2006/0229677 to Moffit
US 2006/0217772 to Libbus
US 2006/0276844 to Alon
US 2007/0196428 to Glauser
US 2007/015009 to Kveen
US 2007/0248676 to Stamler
US 2008/0058872 to Brockway
US 2009/0062874 to Tracey US 2010/0010556 to Zhao
PCT Publication WO 00/002501 to Benjamin
PCT Publication WO 04/014456 to Allen
PCT Publication WO 06/094273 to White
PCT Publication WO 06/064503 to Belsky
PCT Publication WO 06/123346 to Alon
PCT Publication WO 07/064,895 to Meyerhoff
PCT Publication WO 07/106,533 to Stern
PCT Publication WO 07/113,833 to Cahan
PCT Publication WO 07/113,818 to Cahan
PCT Publication WO 08/100,390 to Walker
PCT Publication WO 09/095,918 to Gross
PCT Publication WO 09/095,920 to Gross
European Patent Application Publication EP 0 109 935 A1 to Charmillot
"Vagus nerve stimulation as a method to temporarily slow or arrest the heart," by Matheny, Ann Thorac Surg. 1997 June; 63(6 Suppl):S28-9
"Vagus nerve stimulation decreases left ventricular contractility in vivo in the human and pig heart," by Lewis, J. Physiol. 2001 Jul. 15; 534(Pt 2): 547-552
"Sympathovagal balance is major determinant of short-term blood pressure variability in healthy subjects," by Laitinen, Am J Physiol Heart Circ Physiol 276:1245-1252, 1999
"Preparation and characterization of implantable sensors with nitric oxide release coatings," by M C Frost, Microchemical Journal Vol: 74 Issue: 3, June, 2003 pp: 277-288
"Optimal frequency ranges for extracting information on cardiovascular autonomic control from the blood pressure and pulse interval spectrograms in mice," by Baudrie, Am J Physiol Regul Integr Comp Physiol 292: R904-R912, 2007
"Neural influences on cardiovascular variability: possibilities and pitfalls," by Malpas, Am J Physiol Heart Circ Physiol 282: H6-H20, 2002
"Improving the thromboresistivity of chemical sensors via nitric oxide release: fabrication and in vivo evaluation of NO-releasing oxygen-sensing catheters," by M H Schoenfisch, Anal. Chem., 72 (6), 1119-1126, 2000
"Improving the biocompatibility of in vivo sensors via nitric oxide release," by Jae Ho Shin, Analyst, 2006, 131, 609-615
"Heart rate variability," by Task Force of the European Society of Cardiology and the North American Society of Pacing and Electrophysiology, European Heart Journal (1996) 17, 354-381
"Heart rate and vasomotor control during exercise," by Vallais, Proceedings of the 29th Annual International Conference of the IEEE EMBS, Cite Internationale, Lyon, France, Aug. 23-26, 2007
"Endogenous and exogenous nitric oxide protect against intracoronary thrombosis and reocclusion after thrombolysis," by Sheng-Kun Yao, Circulation. 1995; 92:1005-1010
"Effects of chronic baroreceptor stimulation on the autonomic cardiovascular regulation in patients with drug-resistant arterial hypertension," by Wustmann, Hypertension 2009; 54; 530-536

SUMMARY OF EMBODIMENTS

For some applications of the present invention, a set of one or more electrodes are placed in a vicinity of a first blood vessel (e.g., an artery or a vein) of a subject. A control unit drives a current via the set of electrodes into the wall of the blood vessel, in the vicinity of a bifurcation with a second blood vessel (for example, an artery or a vein). The current is configured to stimulate a contraction in the wall of the first blood vessel, diverting blood flowing through the first blood vessel into the second blood vessel. For some applications, the first and second blood vessels are veins, and the diversion of blood from the first (upstream) vein into the second (downstream) vein enhances downstream blood flow in the first vein. Alternatively, the first and second blood vessels are arteries, and the diversion of blood from the first artery to the second artery enhances perfusion of the second artery, thereby enhancing perfusion of an organ that is supplied by the second artery.

Typically, the set of one or more electrodes comprises a plurality of electrodes disposed at respective locations along the length of the first blood vessel in the vicinity of the bifurcation. The control unit drives the set of electrodes to stimulate peristaltic contractions in the direction of the bifurcation, in order to enhance downstream blood flow in the first blood vessel, and/or enhance perfusion of the second blood vessel.

For some applications, the set of electrodes are placed in the vicinity of the aorta at a site downstream of a bifurcation with one of the carotid arteries. In such applications, the control unit is typically configured to drive a current configured to cause a peristaltic wave of contraction in the wall of the aorta, and this wave of contraction diverts, into the carotid artery, blood that would otherwise have flowed further downstream through the aorta. In an alternative application, the set of electrodes are placed in the vicinity of the aorta at a site downstream of a bifurcation with a renal artery. In such an application the control unit drives a current that causes a peristaltic wave of contraction in the wall of the aorta, and this wave of contraction diverts blood flowing through the aorta into the renal artery of the subject.

For some applications, first and second sets of one or more electrodes are placed in the vicinity of a first blood vessel of the subject, in the vicinity of a bifurcation with a second blood vessel. The first set of electrodes is placed in the vicinity of a site downstream of the bifurcation with the second blood vessel, and the second set of electrodes is placed in the vicinity of a site upstream of the bifurcation with the second blood vessel. For such applications, driving a current into the two sets of electrodes causes contractions to occur on either side of the bifurcation, e.g., waves of peristaltic contractions on either side of the bifurcation, directed toward the bifurcation. These waves of contractions divert blood flowing through the first blood vessel into the second blood vessel of the subject.

For some applications, a set of one or more electrodes described hereinabove is coupled to an outer surface of a catheter. The catheter is advanced in the first blood vessel to a site downstream of a bifurcation with the second blood vessel. The control unit drives a current via the set of electrodes into the wall of the blood vessel, at the site that is downstream of the bifurcation. The current is configured to cause contraction, e.g., a wave of peristaltic contraction in the wall of the blood vessel, diverting blood flowing through the first blood vessel into the second blood vessel.

For some applications, two sets of one or more electrodes are coupled to the outer surface of the catheter. In such an application, the two sets of electrodes are disposed on the catheter such that the first set of electrodes is disposed downstream of, and the second set of electrodes upstream of, the bifurcation with the second blood vessel. The control unit drives a current into the two sets of electrodes, and the current is configured to cause contraction, e.g., waves of peristaltic contraction toward the bifurcation. Due to the positioning of the two sets of electrodes, waves of peristaltic contraction occur on either side of the bifurcation, providing force with which to divert blood flowing through the first blood vessel into the second blood vessel of the subject.

For some applications, techniques described herein are used to treat erectile dysfunction of a subject. Electrodes are placed in a first artery (e.g., the common iliac artery, the internal iliac artery, or the internal pudendal artery), near the bifurcation with a second artery (e.g., the internal iliac artery, the internal pudendal artery, or the dorsal artery of the penis, respectively). Current is applied using techniques described herein in order to enhance blood flow into the second artery.

For some applications, the techniques described herein are used to reduce pressure in a subject's kidney by increasing the diameter of a renal vein. For example, such techniques may be applied to subject's suffering from heart failure, renal failure, and/or hypertension. For some applications pressure in the subject's kidney is reduced via neural pathways. For example, a current may be driven into nerve endings of the subject such that sympathetic activity of the subject is inhibited, and/or such that parasympathetic activity increases.

There is therefore provided, in accordance with some applications of the present invention, apparatus, including:

a mechanical support element configured to be placed inside a first vein of a subject;

at least one electrode disposed on the mechanical support element and configured to be placed inside the first vein, in a vicinity of a site upstream of a bifurcation with a second vein of the subject;

a control unit configured to enhance downstream blood flow from the first vein by driving the at least one electrode to divert blood downstream into the second vein by constricting the first vein at the upstream site, by driving the at least one electrode to apply a current to the vicinity of the site, the mechanical support element being configured to prevent the first vein from collapsing by providing mechanical support to the vein.

For some applications, the mechanical support element includes a shape-memory material, and, subsequent to the control unit constricting the blood vessel, the mechanical support element is configured to dilate the blood vessel by expanding.

For some applications, the mechanical support element includes an elastic material, and, subsequent to the control unit constricting the blood vessel, the mechanical support element is configured to dilate the blood vessel by expanding.

For some applications, the electrode includes two electrodes that are disposed on the mechanical support element such that the electrodes are placed in vicinities of contralateral sides of the first vein by the mechanical support element being placed inside the vein, and the control unit is configured to constrict the vein by driving the current via the electrodes that are disposed on the contralateral sides of the first vein.

For some applications, the control unit is configured to drive the electrode to apply the current irrespective of a phase of a cardiac cycle of the subject.

For some applications, the control unit is configured to drive the electrode to apply the current in pulses, each of the pulse having a duration of 0.5 ms to 10 ms.

For some applications, the control unit is configured to drive the electrode to apply the current in pulses, each of the pulse having a duration of 0.3 ms to 2 ms.

For some applications, the control unit is configured to configure the current to divert blood into the second vein by generating a peristaltic wave of constriction in a downstream direction, along the wall of the first vein.

For some applications, the control unit is configured to drive the electrode to apply the current to the vicinity of the upstream site during systole of the subject.

For some applications, the control unit is configured to withhold driving the current during diastole.

For some applications, the control unit is configured to drive the electrode to apply the current to the vicinity of the upstream site, during diastole of the subject.

For some applications, the control unit is configured to withhold driving the current during systole.

For some applications, the apparatus further includes a sensor configured to sense a level of blood pressure in a vicinity of the bifurcation and to generate a signal in response thereto, and the control unit is configured to receive the signal and to regulate the current in response to the signal.

For some applications, the control unit is configured to identify when the level of the blood pressure is lower than a designated threshold blood pressure level, and to regulate the current in response thereto.

For some applications, to regulate the current the control unit is configured to initiate application of the current or raise a level of the current in response to the sensed level of blood pressure being lower than the threshold level of blood pressure.

For some applications, the control unit is configured to store the threshold, the threshold having a value between 80 and 120 mmHg.

For some applications, the at least one electrode is configured to be implanted, for at least 24 hours, in the first vein of the subject.

For some applications, the at least one electrode is configured to be chronically implanted in the first vein of the subject.

For some applications, the at least one electrode is configured to be implanted in the first vein of the subject for a period of time less than 4 weeks.

For some applications, the at least one electrode is configured to be implanted, for at least 24 hours, in the first vein.

For some applications, the control unit is configured to configure the current to have an amplitude that is between 1 mA and 20 mA.

For some applications, the control unit is configured to configure the current to have an amplitude that is between 3 mA and 10 mA.

For some applications, the control unit is configured to configure the current to have a frequency that is between 10 Hz and 250 Hz.

For some applications, the control unit is configured to configure the current to have a frequency that is between 6 Hz and 20 Hz.

There is further provided, in accordance with some applications of the present invention, a method, including:

driving a first electric current into a vicinity of a site of a first vein of a subject that is upstream of a bifurcation of the first vein with a second vein of the subject;

configuring the electric current to divert blood in a downstream direction, into the second vein, by constricting the first vein at the upstream site; and preventing the first vein from collapsing by providing mechanical support to the vein.

There is additionally provided, in accordance with some applications of the present invention, apparatus, including:

an electrode configured to be placed in an artery of a subject;

a control unit configured to drive the electrode to perform a function with respect to the artery, the function selected from the group consisting of: driving a current into the artery, and sensing an electrical parameter of the artery; and a transmitter configured to be placed in a vein of the subject that is in a vicinity of the artery, the transmitter being wiredly connected to the control unit, and the control unit being configured to drive the electrode by wirelessly transmitting a signal via the transmitter.

For some applications, the transmitter is configured to be placed in the vein such that the transmitter is at a distance of less than 20 mm from the electrode.

For some applications, the transmitter is configured to be placed in a pulmonary vein of the subject, and the electrode is configured to be placed in an aorta of the subject.

There is further provided, in accordance with some applications of the present invention, a method, including:

placing an electrode in an artery of a subject;

placing in a vein of the subject that is in a vicinity of the artery, a transmitter that is wiredly connected to a control unit; and using the control unit, driving the electrode to perform a function with respect to the artery, the function selected from the group consisting of: driving a current into the artery, and sensing an electrical parameter of the artery, the driving being performed by the control unit wirelessly transmitting a signal via the transmitter.

There is additionally provided, in accordance with some applications of the present invention, apparatus, including:

a mechanical support element having a proximal portion and a distal portion, both portions configured to be placed inside a blood vessel of a subject;

a first set of electrodes, disposed in series along the proximal portion of the support element, each electrode disposed at a distance from an adjacent one of the electrodes that is less than 30 mm; and a second set of electrodes, disposed in series along the distal portion of the support element, each electrode in the second set of electrodes disposed at a distance, from an adjacent electrode in the second set of electrodes, that is less than 30 mm, a distal-most electrode in the first set of electrodes and a proximal-most electrode in the second set of electrodes being disposed along the support element at a distance from one another of more than 1 cm.

For some applications, a diameter of the support element is less than 35 mm.

For some applications, the support element includes a catheter.

For some applications, the support element includes a wire frame.

There is further provided, in accordance with some applications of the present invention, apparatus, including:

at least one electrode configured to be placed in a vicinity of a site of a first artery of a subject that is downstream of a bifurcation of the first artery with a second artery of the subject; and a control unit configured to drive the at least one electrode to divert blood in an upstream direction, into the second artery, by constricting the first artery at the downstream site, by driving the at least one electrode to apply a current to the vicinity of the site.

For some applications, the apparatus further includes a housing, the electrode includes two electrodes that are coupled to the housing, the housing is configured to be coupled to the artery such that the electrodes are placed in vicinities of contralateral sides of the first artery, and the control unit is configured to constrict the blood vessel by driving the current via the electrodes that are disposed on the contralateral sides of the first artery.

For some applications, the electrode is configured to be placed inside the first artery.

For some applications, the electrode is configured to be placed outside the first artery.

For some applications, the electrode is configured to be placed in a wall of the first artery.

For some applications, the control unit is configured to drive the electrode to drive the electrode to apply the current irrespective of a phase of a cardiac cycle of the subject.

For some applications, the first artery includes an artery of the subject selected from the group consisting of: a common iliac artery, an internal iliac artery, an internal pudendal artery, and a femoral artery, and the electrode is configured to be placed in a vicinity of the selected artery.

For some applications, the second artery includes an artery of the subject selected from the group consisting of: a common iliac artery, an internal iliac artery, an internal pudendal artery, and a femoral artery, and the control unit is configured to drive the electrode to divert the blood into the selected artery.

For some applications, the control unit is configured to drive the electrode to apply the current in pulses, each of the pulse having a duration of 0.5 ms to 10 ms.

For some applications, the control unit is configured to drive the electrode to apply the current in pulses, each of the pulse having a duration of 0.3 ms to 2 ms.

For some applications, the control unit is configured to drive the electrode to apply the current to the vicinity of the downstream site during systole of the subject.

For some applications, the control unit is configured to withhold driving the current during diastole.

For some applications, the electrode is configured to be implanted in a vicinity of an aorta of the subject, downstream of a right carotid artery of the subject, and the control unit is configured to drive the at least one electrode to apply the current to a vicinity of a site of the aorta of the subject that is downstream of the right carotid artery, to divert the blood into the right carotid artery.

For some applications, the control unit is configured to drive the electrode to apply the current to the vicinity of the downstream site, during diastole of the subject.

For some applications, the control unit is configured to withhold driving the current during systole.

For some applications, the electrode is configured to be implanted in a vicinity of an ascending aorta of the subject, and the control unit is configured to drive the at least one electrode to apply the current to a vicinity of the ascending aorta to divert the blood into a coronary artery of the subject.

For some applications, the apparatus further includes a sensor configured to sense a level of blood pressure in a vicinity of the bifurcation and to generate a signal in response thereto, and the control unit is configured to receive the signal and to regulate the current in response to the signal.

For some applications, the control unit is configured to identify when the level of the blood pressure is lower than a designated threshold blood pressure level, and to regulate the current in response thereto.

For some applications, to regulate the current, the control unit is configured to initiate application of the current or raise a level of the current in response to the sensed level of blood pressure being lower than the threshold level of blood pressure.

For some applications, the control unit is configured to store the threshold, the threshold having a value between 80 and 120 mmHg.

For some applications, the at least one electrode is configured to be implanted, for at least 24 hours, in the vicinity of the first artery of the subject.

For some applications, the at least one electrode is configured to be chronically implanted in the vicinity of the first artery of the subject.

For some applications, the at least one electrode is configured to be implanted in the vicinity of the first artery of the subject for a period of time less than 4 weeks.

For some applications, the at least one electrode is configured to be implanted, for at least 24 hours, in contact with the first artery of the subject.

For some applications, the apparatus further includes a wire frame, the at least one electrode is coupled to the wire frame, and the wire frame is configured to be implanted in the first artery of the subject.

For some applications, the wire frame is configured to be implanted in an ascending aorta of the subject.

For some applications, the wire frame is configured to be implanted in an aorta of the subject downstream of a right carotid artery of the subject.

For some applications,
the at least one electrode includes a first set of electrodes,
the apparatus further includes a second set of electrodes configured to be implanted in a vicinity of a site of the first artery that is upstream of the bifurcation, and the control unit is configured to drive the first and second sets of electrodes to apply respective first and second currents to the vicinities of, respectively, the downstream and upstream sites.

For some applications, the control unit is configured to drive the two sets of electrodes to apply the first current and the second current at the same time.

For some applications,
the apparatus further includes a first and a second wire frame,
the first set of electrodes is coupled to the first wire frame, and the second set of electrodes is coupled to the second wire frame, and
the first wire frame is configured to be implanted at the site downstream of the bifurcation, and
the second wire frame is configured to be implanted at the site upstream of the bifurcation.

For some applications, the control unit is configured to drive the first set of electrodes and the second set of electrodes to apply the first and second currents to the vicinities of the respective sites of the first artery during diastole of the subject.

For some applications, the control unit is configured to configure the current to have an amplitude that is between 1 mA and 20 mA.

For some applications, the control unit is configured to configure the current to have an amplitude that is between 3 mA and 10 mA.

For some applications, the control unit is configured to configure the current to have a frequency that is between 10 Hz and 250 Hz.

For some applications, the control unit is configured to configure the current to have a frequency that is between 6 Hz and 20 Hz.

For some applications, the apparatus further includes a catheter, and the electrode is coupled to the catheter.

For some applications, the at least one electrode includes a first set of electrodes, the apparatus further including a second set of electrodes, the first and second sets of electrodes being coupled to the catheter.

For some applications, the first artery includes an aorta of the subject, and the catheter is configured to be advanced within the aorta.

For some applications, the catheter is configured to be advanced within the first artery to the downstream site, and the electrode is configured to be at the downstream site when the control unit drives the electrode to apply the current.

For some applications, the control unit is configured to configure the current to divert blood into the second artery by generating a peristaltic wave of constriction in an upstream direction, along the wall of the first artery.

For some applications,
the at least one electrode includes a first set of electrodes configured to be placed downstream of the bifurcation,
the apparatus further includes a second set of electrodes configured to be placed upstream of the bifurcation, and
the control unit is configured to divert blood into the second artery by:
generating a peristaltic wave of constriction in an upstream direction, along the wall of the first artery, by driving the first set of electrodes to apply a first current to the wall of the first artery, and
generating a peristaltic wave of constriction in a downstream direction, along the wall of the first artery, by driving the second set of electrodes to apply a second current to the wall of the first artery.

For some applications, the first artery includes an aorta of the subject, and the at least one electrode is configured to be placed in a vicinity of an aortic site that is downstream of a bifurcation of the aorta with a second artery of the subject.

For some applications, the second artery includes a carotid artery of the subject, and the control unit is configured to divert blood into the carotid artery of the subject by driving the electrode to apply the current to the vicinity of the aortic site.

For some applications, the second artery includes a renal artery of the subject, and the control unit is configured to divert blood into the renal artery of the subject by driving the electrode to apply the current to the vicinity of the aortic site.

For some applications, the second artery includes a coronary artery of the subject, and the control unit is configured to divert blood into the coronary artery of the subject by driving the electrode to apply the current to the vicinity of the aortic site.

There is additionally provided, in accordance with some applications of the present invention, a method, including:
driving a first electric current into a vicinity of a site of a first artery of a subject that is downstream of a bifurcation of the first artery with a second artery of the subject; and
configuring the electric current to divert blood in an upstream direction, into the second artery, by constricting the first artery at the downstream site.

The present invention will be more fully understood from the following detailed description of embodiments thereof, taken together with the drawings, in which:

BRIEF DESCRIPTION OF THE DRAWINGS

FIG. 1C is a schematic illustration of a blood diverting device, in accordance with yet another application of the present invention;

FIG. 2C is a schematic illustration of the blood diverting device of FIG. 1C implanted in the aorta in the vicinity of the renal arteries, in accordance with some applications of the present invention;

FIG. 4 is a schematic illustration of a blood diverting device implanted inside a vein, in accordance with some applications of the present invention;

FIGS. 8A-D are graphs showing the tension measured in an aortic ring in response to electrical stimulation (FIG. 8A-B), and in response to the administration of substance P neuropeptide (FIGS. 8C-D).

DETAILED DESCRIPTION OF EMBODIMENTS

Figure 1A:
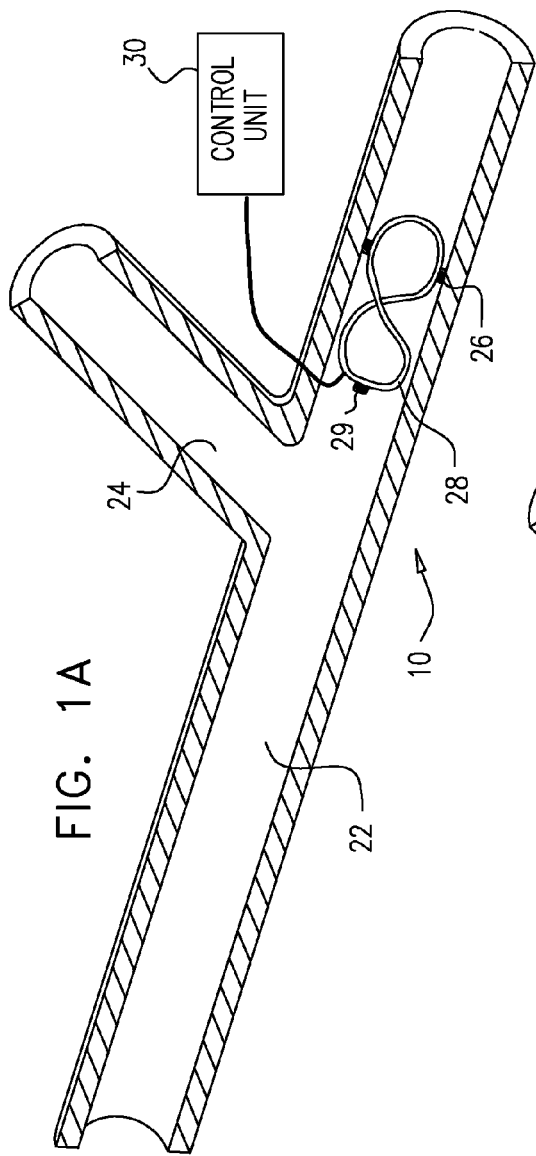
FIG. 1A is a schematic illustration of a blood diverting device, in accordance with some applications of the present invention.

Reference is now made to FIG. 1A, which is a schematic illustration of a blood diverting device 10, in accordance with some applications of the present invention. Blood diverting device 10 comprises an electrode 26 coupled to a wire frame 28. A control unit 30, coupled to wire frame 28, is configured to drive electrode 26 to apply an electric current to a local portion of the wall of a first blood vessel 22, causing contraction of this portion of the wall of first blood vessel 22. Contraction of the wall of first blood vessel 22 diverts blood away from first blood vessel 22 into a second blood vessel 24 of the subject, enhancing the perfusion of second blood vessel 24.

Typically, but not necessarily, at least a portion of blood diverting device 10 is designated for implantation into first blood vessel 22 of the subject. When blood vessel 22 is an artery, blood diverting device 10 is typically implanted within first blood vessel 22 at a site that is downstream with respect to the bifurcation with second blood vessel 24 of the subject. (In the context of the present patent application and in the claims, the words "upstream" and "downstream" are to be understood as being with respect to the natural direction of blood flow.) For some applications, blood diverting device 10 is designated for implantation for a relatively short period, e.g., up to about one month (for example, two weeks). Alternatively, blood diverting device 10 is designated for chronic implantation, i.e., for a period of greater than one month.

For some applications, control unit 30 stimulates contraction of a portion of the wall of first blood vessel 22 by driving an electric current with an amplitude of more than 1 mA, and/or less than 20 mA (e.g., 1-20 mA) into a portion of the wall of first blood vessel 22. Typically, the electric current has a frequency of more than 10 Hz, and/or less than 250 Hz (e.g., 10-250 Hz). The electric current is typically driven in a series of pulses, each having a duration of more than 0.5 and/or less than 10 ms (e.g., 0.5-10 ms). For some applications, the control unit drives a current having an amplitude of 3 mA to 10 mA, a frequency of 6 Hz to 20 Hz, and a pulse duration of 0.3 ms to 2 ms. In accordance with respective applications of the invention, the current may be driven in a biphasic, monophasic, symmetric and/or asymmetric pulse. For some applications, the control unit causes the blood vessel to contract by stimulating a nerve, by driving the current into the first blood vessel. For some applications, the control unit drives the current into a third blood vessel that is located in a vicinity of the first blood vessel in order to cause the first blood vessel to contract.

For some applications, control unit 30 detects the subject's cardiac cycle and drives the current in coordination with the subject's cardiac cycle. Alternatively, the control unit drives the current irrespective of the phase of the subject's cardiac cycle. Although some applications are described herein according to which the control unit drives the current during a specific phase of the cardiac cycle, the scope of the present invention includes the control unit driving the current during an alternative phase of the cardiac cycle, or not in coordination with the cardiac cycle.

For some applications, a blood pressure sensor 29 is coupled to blood diverting device 10, and is configured to detect the blood pressure of the subject at a particular location within the body of the subject, for example, at or adjacent to the bifurcation of first blood vessel 22 and second blood vessel 24. Blood pressure sensor 29 measures the blood pressure of the subject and sends a signal to control unit 30. Upon receiving the signal from blood pressure sensor 29, control unit 30 adjusts the amplitude of the current in accordance with the sensed blood pressure of the subject. For example, control unit 30, on receiving a sensed blood pressure with a value below 80 mmHg, may increase the amplitude of the current by more than 10% and/or less than 50%, e.g., 10-50%, and sense the pressure at the bifurcation again after having increased the current amplitude. Alternatively, having sensed a blood pressure with a value above 80 mmHg, control unit 30 may decrease the amplitude of the current by more than 10% and/or less than 50%, e.g., 10-50%. As appropriate, the threshold value of 80 mmHg may be varied depending on the anatomical location sensed and the state of the patient. For some applications, the threshold value is more than 80 mmHg and/or less than 120 mmHg, e.g., 80-120 mmHg.

For some applications, parameters of the subject are detected via an impedance sensor, a pressure sensor (e.g., for sensing wedge pressure), a breathing sensor, and/or a fluid sensor, and blood diverting device 10 operates in a closed-loop cycle, responsively to the parameters detected by the sensor. For some applications, one or more of the aforementioned sensors sense parameters of the subject's left ventricle and/or left atrium.

Typically, all of electrodes 26 are disposed on (e.g., wrapped around) wire frame 28. For some applications, wire frame 28 is made of nitinol, and/or the electrodes are made of platinum iridium. For some applications, sensing electrodes are disposed on the wire frame. The sensing electrodes are typically separated from the stimulation electrodes, in order to prevent the stimulation signal from interfering with the signal that is detected by the sensing electrodes.

For some applications, control unit 30 drives electrodes 26 wirelessly. For example, an antenna may be disposed on wire frame 28 and the control unit drives the electrodes wirelessly via the antenna that is disposed on the wire frame. Or, the wire frame may include a piezoelectric element that is driven by an ultrasound transducer that is outside the subject's body. For some applications, the control unit is not implanted inside the subject's body but is worn, or otherwise disposed, outside the subject's body. Alternatively, the control unit, in addition to the electrodes, is implanted inside the subject's body.

For some applications, control unit 30 transmits a signal for driving the electrodes via a transmitter (e.g., a transmitting coil) that is placed inside a vein of the subject. For example, the control unit may be implanted inside the subject's body, and/or outside the subject's body, and wiredly coupled to the transmitter. The transmitter may be placed in the subject's pulmonary vein (or another vein) and a signal may be driven via the transmitter to an antenna disposed on wire frame 28, the wire frame being disposed in the subject's aorta.

The scope of the present invention includes driving with a control unit any stimulating or sensing electrodes that are disposed in an artery of a subject, via a transmitter (e.g., a transmitting coil) that is wiredly connected to the control unit and that is placed inside a vein that is in the vicinity of the artery. For example, the electrodes may be placed in the aorta, a carotid artery, a subclavian artery, and/or the pulmonary artery, and the transmitter may be placed in the pulmonary vein, innominate vein, vena cava, jugular vein, and/or subclavian vein. Typically, the transmitter is placed inside the vein such that it is at a distance from the intra-arterial electrodes of more than 5 mm and/or less than 20 mm, e.g., 5-20 mm. Typically, placement of the transmitter in the vein facilitates transmission of the signal from the control unit to the electrodes, due to the proximity of the vein to the artery in which the electrodes are placed. Further typically, the dimensions of the vein are such that the vein is able to accommodate a transmitting coil, even in the absence of a rigid housing for housing the coil.

Figure 1B:
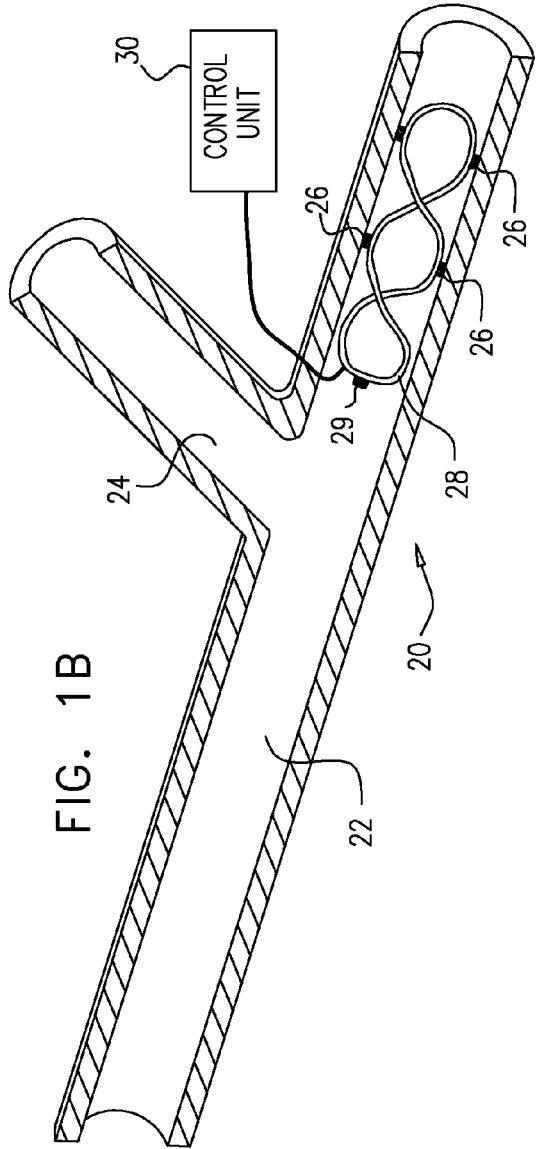
FIG. 1B is a schematic illustration of a blood diverting device, in accordance with another application of the present invention.

Reference is now made to FIG. 1B, which is a schematic illustration of a blood diverting device 20, in accordance with some applications of the present invention. Blood diverting device 20 is generally similar to blood diverting device 10 as described hereinabove with reference to FIG. 1A, except for differences as described hereinbelow. Blood diverting device 20 comprises a plurality of electrodes 26 coupled to wire frame 28. In such applications, control unit 30 drives a current into the plurality of electrodes 26. The current is configured to cause contraction of the wall of first blood vessel 22. For example, the control unit may drive each one of electrodes 26 in sequence, from the most downstream electrode 26 toward the most upstream electrode 26, in order to generate a wave of peristaltic contraction in the wall of first blood vessel 22, thereby diverting blood into second blood vessel 24 of the subject.

For some applications, first and second electrodes 26 are placed within blood vessel 22 at a longitudinal distance from each other of between 10 mm and 30 mm and/or at a radial distance from each other of less than 10 degrees. Alternatively, the first and second electrodes 26 are placed within blood vessel 22 at a longitudinal distance from each other of between 2 mm and 10 mm. For some applications ten or more electrodes (for example, 20 electrodes) are implanted inside blood vessel 22. For some applications, the electrodes are oriented to have a surface area of between 3 mm2 and 15 mm2, e.g. between 5 mm2 and 12 mm2, in contact with tissue of blood vessel 22.

Typically, the electrodes are configured to induce contraction of blood vessel 22 by a current being driven via respective electrodes with a spacing in time of 10 ms to 50 ms. For some applications, the electrodes are disposed longitudinally along the blood vessel with a longitudinal spacing therebetween of 150%-250% of the local diameter of the blood vessel, and/or of 1-5 cm. The spacing may be maintained, for example, by wire frame 28 (as shown), by a housing to which the electrodes are coupled (e.g., a flexible stent), or by sutures or adhesives which couple the electrodes to the aorta. As appropriate for the level of peristaltic flow desired, the time for a peristaltic wave to be generated and to travel from the most downstream of the most upstream electrode (or in the opposite direction) typically ranges from 0.25 second to about 2 seconds. Typically, a current having the same parameters is driven via each of the electrodes. For some applications, a current having a first set of parameters is driven via a first one of electrodes 26, and a current having a second set of parameters is driven via a second one of the electrodes.

For some applications, wire frame 28 is highly flexible and/or has a different configuration from the figure-of-eight configuration shown in the figures. For some applications, electrodes 26 are not disposed on a wire frame. For example, the electrodes may be implanted on the inside and/or the outside of blood vessel 22, and/or within the wall of the blood vessel. For some applications, the electrodes are not placed in direct contact with the blood vessel, but are implanted in the vicinity of the blood vessel, and/or in contact with, or in the vicinity of, a nerve that innervates the blood vessel. For example, the electrodes may be driven to stimulate parasympathetic nerve endings in order to induce relaxation of the blood vessel, and/or sympathetic nerve endings in order to induce contraction of the blood vessel. For some applications, monopolar electrodes are used to drive a current into the blood vessel.

Reference is now made to FIG. 1C, which is a schematic illustration of a blood diverting device 40, in accordance with some applications of the present invention. Blood diverting device 40 is generally similar to blood diverting device 10 and blood diverting device 20, as described hereinabove with reference to FIG. 1A and FIG. 1B, except for differences as described hereinbelow.

Blood diverting device 40 comprises a first and a second set of one or more electrodes 26, coupled to a first wire frame 28 and a second wire frame 28 respectively. Typically, the first wire frame 28 is implanted into first blood vessel 22 at a site downstream of the bifurcation with second blood vessel 24, and the second wire frame 28 is implanted into first blood vessel 22 at a site upstream of the bifurcation with second blood vessel 24. For some applications, each of the wire frames 28 comprises a single electrode. For some applications, a single wire frame acts as a support element for the first and the second sets of the electrodes. The first and second sets of electrodes are disposed respectively on downstream (e.g., proximal) and upstream (e.g., distal) portions of the wire frame.

Control unit 30 is configured to drive a first current via the first set of electrodes 26 and a second current via the second set of electrodes 26. The first current and the second current are configured to cause contraction of the wall of first blood vessel 22. For example, control unit 30 may drive the first current sequentially into each one of electrodes 26 coupled to the first wire frame, from the most downstream electrode 26 toward the most upstream electrode 26, in order to generate a wave of peristaltic contraction in the wall of first blood vessel 22 downstream of the bifurcation with second blood vessel 24. Additionally, control unit 30 may drive the second current sequentially into each one of electrodes 26 coupled to the second wire frame, from the most upstream electrode 26 toward the most downstream electrode 26, in order to generate a wave of peristaltic contraction in the wall of first blood vessel 22 upstream of the bifurcation with second blood vessel 24. These two waves of contraction generated at generally the same time on either side of the bifurcation with second blood vessel 24, towards the bifurcation with second blood vessel 24, increase the pressure of the blood between first and second wire frames 28, thereby diverting blood into second blood vessel 24.

Typically, control unit 30 is configured to drive the first current and the second current into the first and the second set of electrodes 26 at substantially the same time. Alternatively, the control unit applies the first and second currents at slightly different times, but typically within one heartbeat of each other.

Figure 2A:
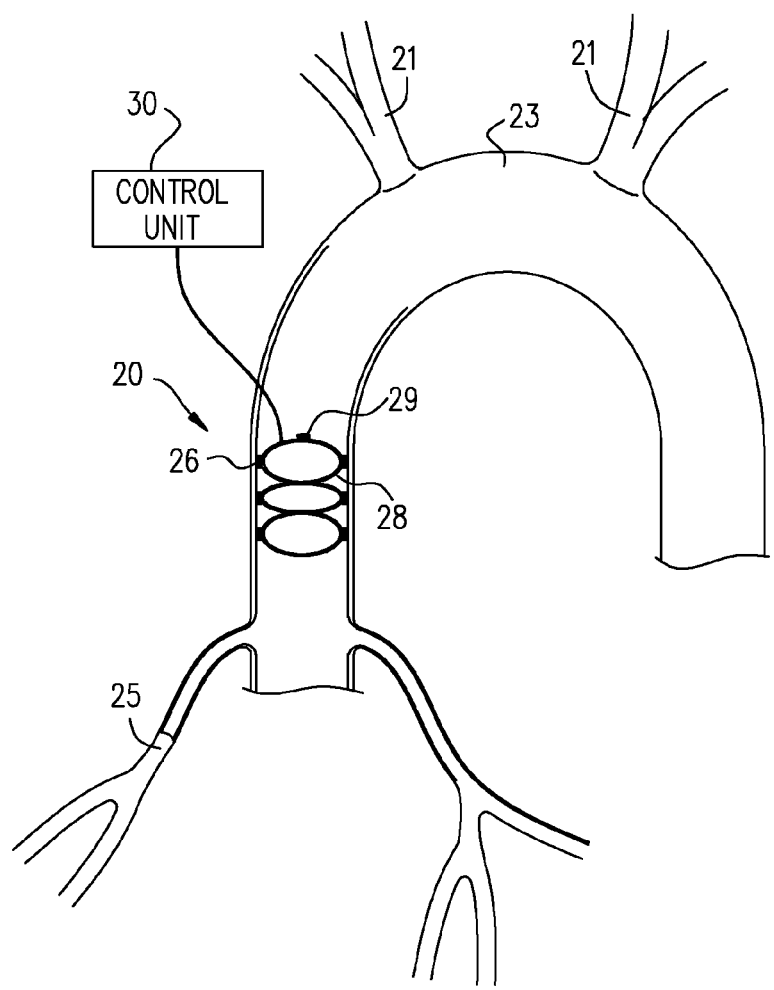
FIG. 2A is a schematic illustration of the blood diverting device of FIG. 1B implanted in the aorta in the vicinity of the coronary arteries, in accordance with some applications of the present invention.

Reference is now made to FIG. 2A, which is a schematic illustration of blood diverting device 20 as described hereinabove with reference to FIG. 1B, implanted in aorta 23 of the subject in the vicinity of a coronary artery 25 of the subject, in accordance with some applications of the present invention.

Blood diverting device 20 is designated for implantation within aorta 23 at a site downstream of the bifurcation with the right and left coronary arteries 25. Control unit 30 drives a current into electrodes 26 during diastole configured to cause contraction of the wall of aorta 23 downstream of the bifurcation with the right and the left coronary arteries 25. For example, the control unit may drive each one of electrodes 26 in sequence, from the most downstream electrode 26 toward the most upstream electrode 26, in order to generate a wave of peristaltic contraction in the wall of aorta 23, thereby diverting blood into coronary arteries 25 of the subject. For some applications, device 20 does not generate a wave of peristaltic contraction, but instead generally simultaneously constricts the portion of aorta 23 affected by the current, whereby some blood flows from the aorta into coronary arteries 25.

Figure 2B:
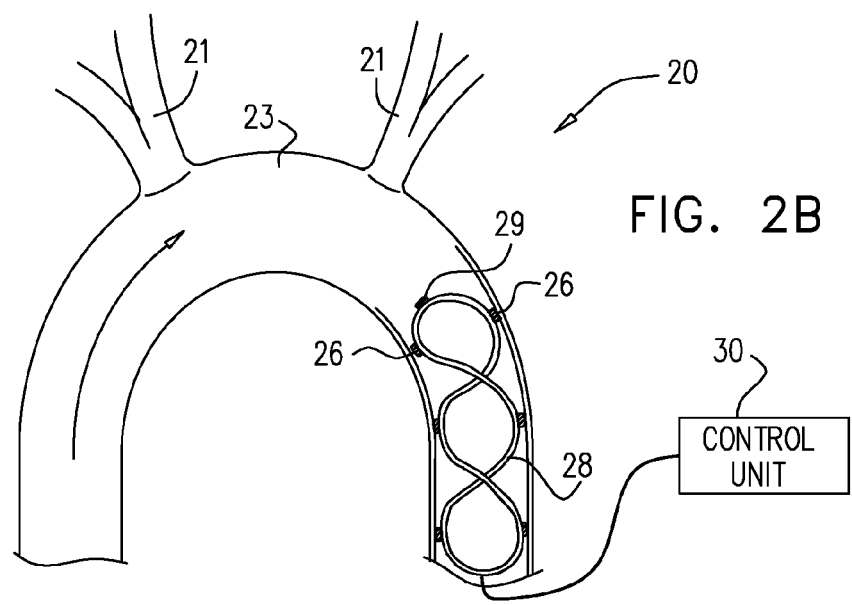
FIG. 2B is a schematic illustration of the blood diverting device of FIG. 1B implanted in the aorta in the vicinity of the carotid arteries, in accordance with some applications of the present invention.

Reference is now made to FIG. 2B, which is a schematic illustration of blood diverting device 20 as described hereinabove with reference to FIG. 1B, implanted in aorta 23 of the subject in the vicinity of right and left carotid artery 21 of the subject, in accordance with some applications of the present invention.

Blood diverting device 20 is designated for implantation into aorta 23 of the subject at a site downstream of the bifurcation with left carotid artery 21. Control unit 30, drives a current into electrodes 26 during systole, configured to generate contraction of the wall of aorta 23 downstream of the bifurcation with left carotid artery 21, using techniques described hereinabove with respect to FIG. 1B. For example, control unit 30 may drive each one of electrodes 26 in sequence, from the most downstream electrode 26 toward the most upstream electrode 26, in order to generate a wave of peristaltic contraction in the wall of aorta 23, thereby diverting blood into carotid arteries 21 of the subject. Alternatively, control unit 30 drives a current that does not induce a peristaltic wave of contraction, but instead generates a single contraction, typically during systole, in order to increase blood pressure upstream of wire frame 28, and thereby enhance blood flow to carotid arteries 21.

For instances in which flow to the left carotid artery 21 is sufficient and it is desired to enhance blood flow to the right carotid artery 21, wire frame 28 is typically placed near the top of the aortic arch, between the left and right carotid arteries.

For some applications, a second wire frame 28 (or a second set of electrodes 26, which are not disposed on a wire frame) is designated for implantation within aorta 23 at a site upstream of the bifurcation with right carotid artery 21, as described hereinabove with respect to FIG. 1C. Control unit 30, drives a current into the plurality of electrodes 26 configured to cause contraction of the wall of aorta 23 upstream of the bifurcation with right carotid artery 21 of the subject, thereby diverting blood into carotid arteries 21 of the subject using techniques described hereinabove with respect to FIG. 1C. For example, the control unit may drive each one of electrodes 26 in sequence, from the most upstream electrode 26 toward the most downstream electrode 26, in order to generate a wave of peristaltic contraction in the wall of aorta 23. The waves of contraction generated by the two wire frames increase blood pressure at the top of the aortic arch, thereby diverting blood into the right and left carotid arteries 21 of the subject. For such applications, the two peristaltic waves are typically generated during diastole.

Reference is now made to FIG. 2C, which is a schematic illustration of blood diverting device 40 as described hereinabove with reference to FIG. 1C, implanted within aorta 23 of the subject in the vicinity of a renal artery 74 of the subject, in accordance with some applications of the present invention. It is noted that placement of device 40 in the vicinity of renal artery 74 is shown by way of illustration and not limitation, and the scope of the present invention includes placement of device 40 at any site downstream of the right carotid artery 21 (e.g., between the right and left carotid arteries, slightly downstream of the left carotid artery 21, or in the vicinity of another artery, such as renal artery 74).

Blood diverting device 40 comprises a first and a second set of one or more electrodes 26, which are typically coupled to a first wire frame 28 and a second wire frame 28 respectively. Typically, the first wire frame 28 (or a set of electrodes 26, which are not disposed on a wire frame) is implanted within aorta 23 at a site downstream of the aortic bifurcation with renal arteries 74, and the second wire frame 28 (or a second set of electrodes 26, which are not disposed on a wire frame) is implanted within aorta 23 at a site upstream of the bifurcation with renal arteries 74. (For some applications, the first and second sets of electrodes are disposed on proximal and distal portions of a single support element (e.g., a single wire frame).) Control unit 30 is configured to drive a first current via the first set of electrodes 26 and a second current via the second set of electrodes 26. The first and the second current are configured to cause contraction of the wall of aorta 23 upstream of the bifurcation and downstream of the bifurcation with renal arteries 74, increasing blood pressure at the bifurcation, and thereby diverting blood into renal arteries 74 of the subject.

For some applications, only a first wire frame is implanted into aorta 23 downstream of the bifurcation with renal arteries 74, as described hereinabove with respect to FIG.

1B. In such applications, control unit 30 drives a current into the plurality of electrodes 26 during systole or during diastole to generate contraction of the wall of aorta 23 downstream of the bifurcation with renal arteries 74. For example, control unit 30 may drive each one of electrodes 26 in sequence, from the most downstream electrode 26 toward the most upstream electrode 26, in order to generate a wave of peristaltic contraction in the wall of aorta 23, thereby diverting blood into renal arteries 74 of the subject. Alternatively, control unit 30 drives a current that does not induce a peristaltic wave of contraction, but instead generates a single contraction at the wire frame 28 that is downstream of the bifurcation, typically during systole, in order to increase blood pressure upstream of wire frame 28, and thereby enhance blood flow to renal arteries 74.

Figure 3A:
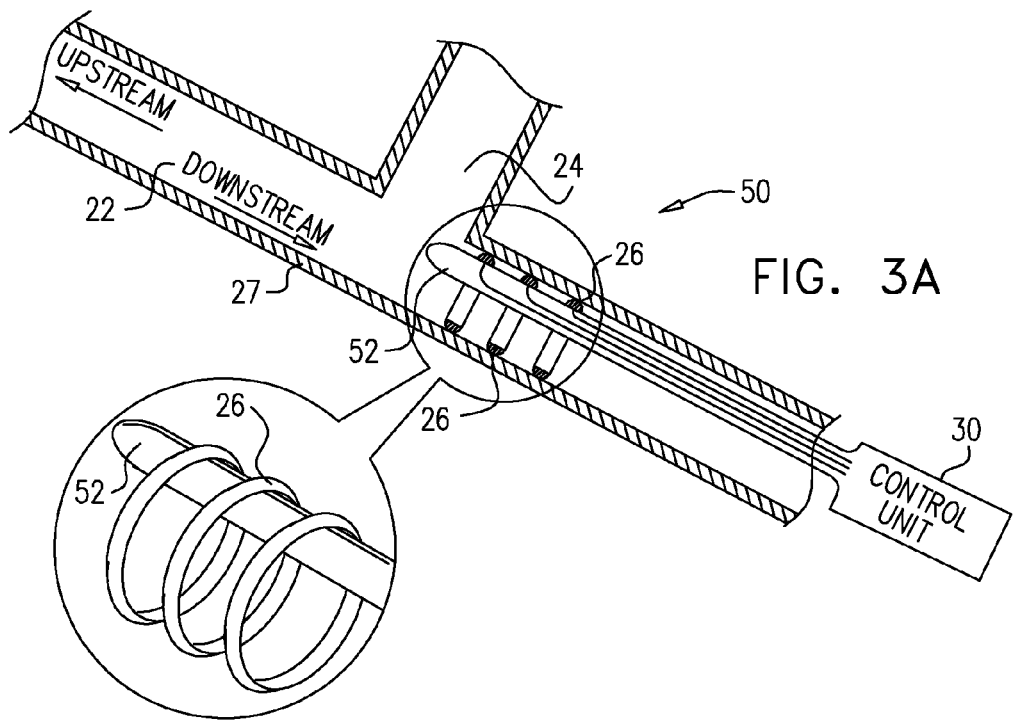
FIG. 3A is a schematic illustration of a blood diverting device, in accordance with some applications of the present invention.

Reference is now made to FIG. 3A, which is a schematic illustration of a blood diverting device 50, in accordance with some applications of the present invention. Blood diverting device 50 is generally similar to blood diverting device 20, as described hereinabove with reference to FIG. 1A, except for differences as described hereinbelow.

Blood diverting device 50 comprises one or more electrodes 26 coupled to a support element, e.g., catheter 52. Catheter 52 is advanced within first blood vessel 22 of the subject. Typically, catheter 52 has a diameter of less than 35 mm. For some applications, when blood vessel 22 is an artery, catheter 52 is advanced within first blood vessel 22 to a site downstream of second blood vessel 24 (i.e., further from the heart), positioning electrodes 26 downstream of the bifurcation with second blood vessel 24, as shown. In such applications, control unit 30 drives a current into electrodes 26 that is configured to cause contraction of the wall of first blood vessel 22. For example, control unit 30 may drive each one of electrodes 26 in sequence, from the most downstream electrode toward the most upstream electrode 26, in order to generate a wave of peristaltic contraction in the wall of first blood vessel 22, thereby increasing blood pressure at the bifurcation and diverting blood into second blood vessel 24. For some applications, first blood vessel 22 includes an aorta of the subject. For some applications, second blood vessel 24 includes a carotid artery of the subject. For other applications, second blood vessel 24 includes a renal artery of the subject. In an alternative application, second blood vessel 24 includes a coronary artery of the subject. Alternatively, control unit 30 drives a current that does not induce a peristaltic wave of contraction, but instead generates a single contraction of first blood vessel 22 downstream of the bifurcation, typically during systole, in order to increase blood pressure at the bifurcation, and thereby enhance blood flow to second blood vessel 24.

Figure 3B:
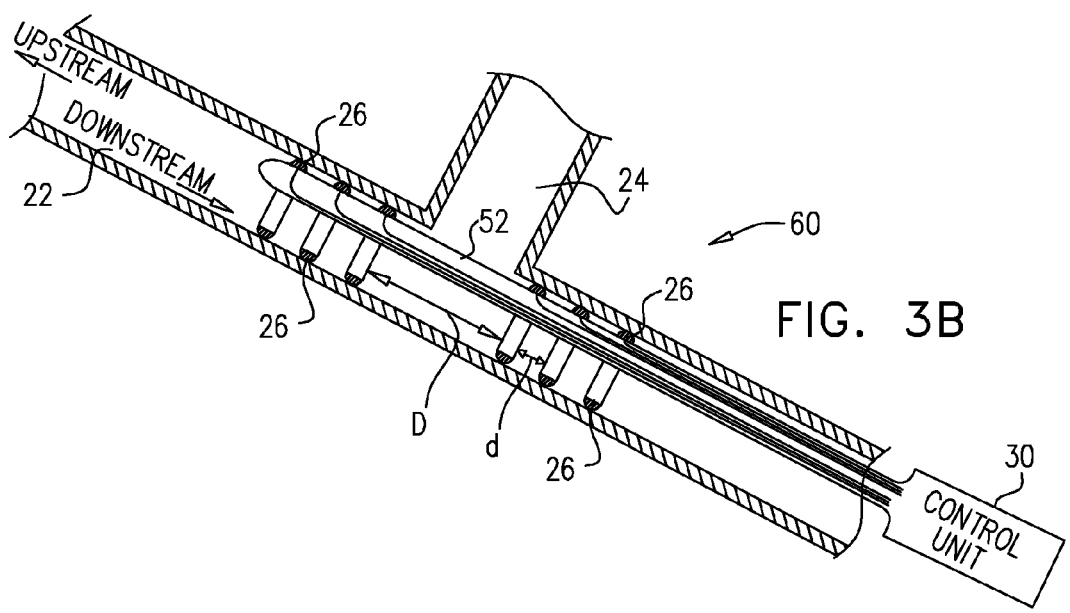
FIG. 3B is a schematic illustration of a blood diverting device, in accordance with another application of the present invention.

Reference is now made to FIG. 3B, which is a schematic illustration of a blood diverting device 60, in accordance with some applications of the present invention. Blood diverting device 60 is generally similar to blood diverting device 40, as described hereinabove with reference to FIG. 1C, except for differences as described hereinbelow.

Blood diverting device 60 comprises a first and a second set of one or more electrodes 26 coupled to proximal and distal portions of a support element, e.g., catheter 52. For some applications, when blood vessel 22 is an artery, catheter 52 is advanced into first blood vessel 22 such that the proximal portion of the catheter and the first set of electrodes 26 are positioned downstream of the bifurcation with second blood vessel 24 (i.e., further from the heart, to the lower right in the figure), and the distal portion of the catheter and the second set of electrodes 26 are positioned upstream of the bifurcation with second blood vessel 24, as shown.

Control unit 30 is configured to drive a first current via the first set electrodes 26 and a second current via the second set of electrodes 26. The first current and the second current are configured to cause contraction of the wall of first blood vessel 22, downstream of the bifurcation with second blood vessel 24 and upstream of the bifurcation with second blood vessel 24, respectively. For example, control unit 30 may drive the first current sequentially into each one of electrodes 26 in the first set of electrodes 26, from the most downstream electrode 26 toward the most upstream electrode 26, in order to generate a wave of peristaltic contraction in the wall of first blood vessel 22 downstream of the bifurcation with second blood vessel 24. Control unit 30 may also drive the second current sequentially into each one of electrodes 26 in the second set of electrodes 26, from the most upstream electrode 26 to the most downstream electrode 26, in order to generate a wave of peristaltic contraction in the wall of first blood vessel 22 upstream of the bifurcation with second blood vessel 24. These two waves of contraction generated on either side of the bifurcation with second blood vessel 24 increase pressure at the bifurcation, and thereby divert blood into second blood vessel 24.

Typically, in accordance with the applications described hereinabove, electrodes belonging to each of the sets of electrodes 26 are disposed longitudinally along catheter 52 with a longitudinal spacing d from an adjacent electrode of the set of electrodes of more than 10 mm and/or less than 30 mm, e.g., 10-30 mm. For some applications, electrodes belonging to each of the sets of the electrodes 26 are disposed longitudinally along catheter 52 with a longitudinal spacing d from an adjacent electrode of the set of electrodes of more than 2 mm and/or less than 10 mm, e.g., 2-10 mm. Further typically, a distal-most electrode in the first set of electrodes and a proximal-most electrode in the second set of electrodes are disposed at a longitudinal distance D from one another of more than 1 cm and/or less than 5 cm, e.g., 1-5 cm. For some applications, the distal-most electrode in the first set of electrodes and the proximal-most electrode in the second set of electrodes are disposed at a longitudinal distance D from one another of more than 10 cm and/or less than 30 cm, e.g., 10-30 cm.

Reference is now made to FIG. 4, which is a schematic illustration of blood diverting device 10 inside blood vessel 22, the blood vessel being a vein, in accordance with some applications of the present invention. Although device 10 is shown in FIG. 4, the scope of the present invention includes using, to apply a current to vein 22, any of devices 20, 40, 50, or 60, and/or any other apparatus and techniques described herein. In accordance with respective applications, vein 22 is a jugular vein, subclavian vein, pulmonary vein, and/or the vena cava.

For some applications, blood flows from an organ of the subject, in the direction of arrow 70, through first vein 22, and to the subject's heart (directly or indirectly) via second vein 24. Device 10 causes vein 22 to contract (typically, peristaltically), using the techniques described herein. The contraction of blood vessel 22 causes the blood flow in the downstream direction, i.e., into blood vessel 24, be enhanced. Typically, this lowers the pressure inside vein 22, which causes more blood to flow from the organ into blood vessel 22, in the direction of arrow 70. In this manner, perfusion of the organ is increased. Alternatively or additionally, this technique is used to enhance venous return from the legs. The scope of the present invention includes using any of the devices or techniques described hereinabove, to increase the blood flow from first vein 22 to second vein 24.

For some applications, wire frame 28, or a different mechanical element (such as a spring, a stent, or a different wire frame), is configured to prevent the vein from collapsing during the constriction of the vein, and/or to restore the shape of first vein 22 after the vein has been contracted. For example, wire frame 28 may be made of a shape-memory alloy, such as nitinol, that is configured to assume an expanded shape, when not being constrained by the contraction of vein 22. The expansion of the shape-memory alloy causes the vein to expand and assume its original shape, and facilitates refilling of the vein and perfusion of the organ upstream of the site of wire frame 28. Alternatively, wire frame 28 may be made of an elastic material that is configured to assume an expanded shape, when not being constrained by the contraction of vein 22.

Figure 5B:
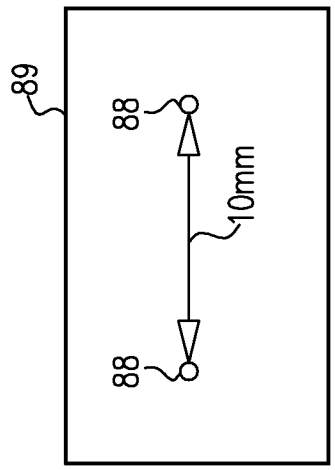
FIGS. 5A-B are schematic illustrations of a set-up of an experiment that was conducted in accordance with an application of the present invention.
Figure 5A:
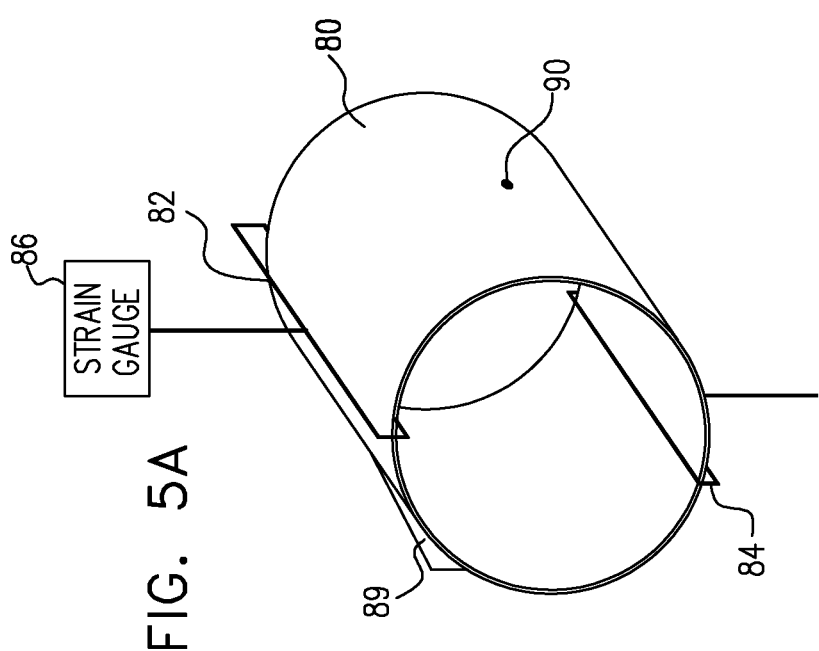

Reference is now made to FIGS. 5A-B, which are schematic illustrations of apparatus that was used in an experiment that was conducted in accordance with an application of the present invention. A 15 mm ring 80 of an aorta was dissected from a pig, and was held in place using upper and lower support elements 82 and 84. Upper support element 82 was connected to a strain gauge 86, such that the strain gauge measured the tension in the aortic ring. Two unipolar epicardial electrodes (Medtronic CapSure Epi 4965) were placed on the adventitia of the aortic ring on one side of the aortic ring (i.e., ipsilaterally to each other, with respect to the aortic ring). The ipsilateral electrodes were coupled to one another by a custom made support 89 (shown in FIG. 5B), at a longitudinal distance of 10 mm from one another. Another electrode 90 was placed on the adventitia of the aortic ring on the side of the aortic ring contralateral to the side on which electrodes 88 were placed.

Aortic ring 80 was electrically stimulated during respective time periods by (a) driving a current into the aortic ring via the two ipsilateral electrodes 88, and (b) driving a current into the aortic ring via one of electrodes 88 and contralateral electrode 90. The current was driven at an amplitude of 15 mA, with a frequency of 50 Hz, and with a pulse width of 4 ms. The tension in the aortic ring before, during, and after stimulation of the aortic ring by the electrodes was measured.

Figure 6A:
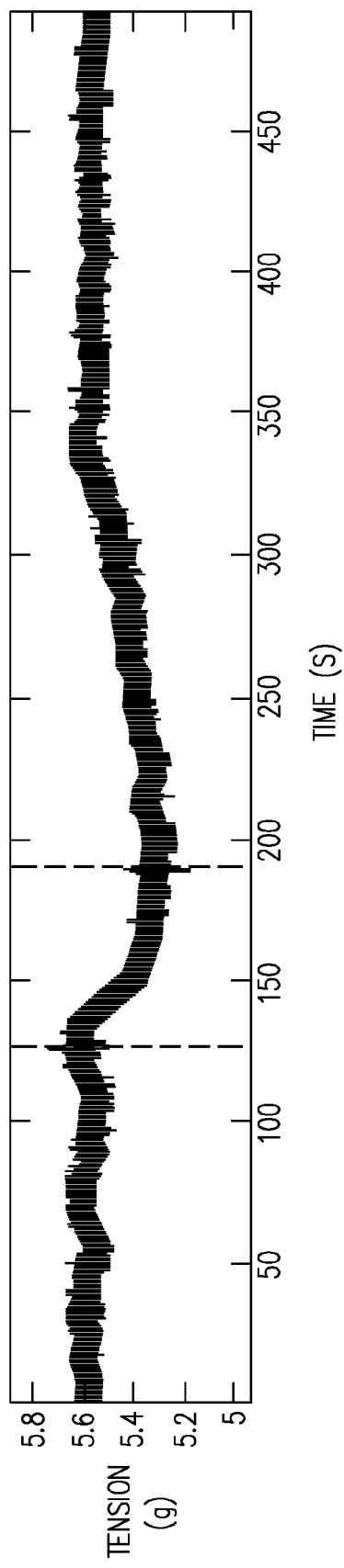
FIGS. 6A-B are graphs showing the tension that was measured in an aortic ring before, during and after stimulation of the ring by, respectively, two ipsilaterally disposed electrodes (FIG. 6A), and two contralaterally disposed electrodes (FIG. 6B)
Figure 6B:
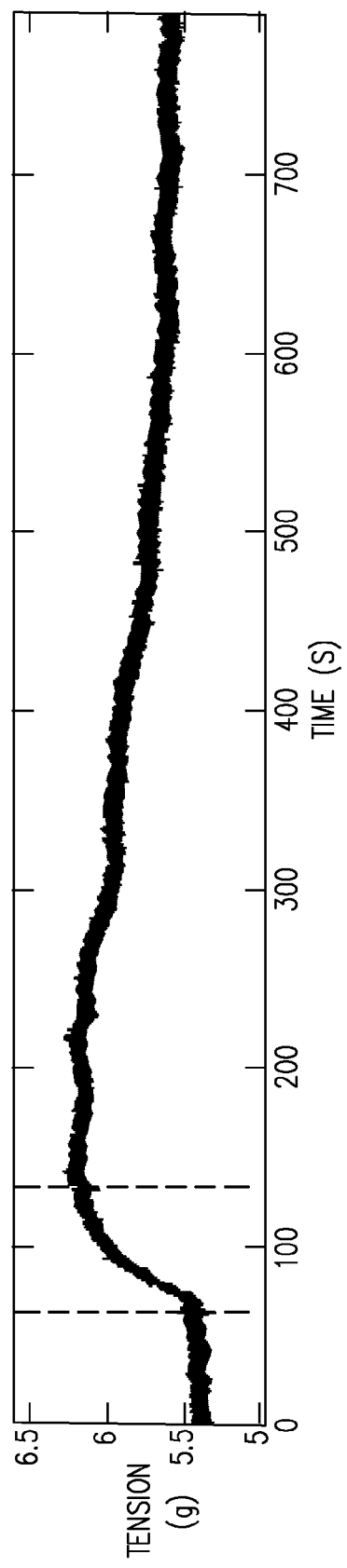

Reference is now made to FIGS. 6A-B, which are graphs showing the tension that was measured in aortic ring 80 before, during and after stimulation of the ring by, respectively, the two ipsilateral electrodes (FIG. 6A), and contralateral electrodes (FIG. 6B). The beginning and end of the stimulation periods are denoted by the vertical dashed lines in the graphs.

It may be observed that stimulation of the aortic ring with the ipsilateral electrodes (FIG. 6A) resulted in a decrease in the tension of the aortic ring. The aortic ring recovered its pre-stimulation level of tension about 150 seconds after the stimulation period finished. Stimulation of the aortic via contralateral electrodes (FIG. 6B) resulted in an increase in the tension of the ring. These results indicate that stimulating the aorta, and/or other arteries, using electrodes that are disposed ipsilaterally, and longitudinally with respect to one another causes a decrease in the tension in the arterial wall, i.e., the artery dilates. Stimulating the aorta, and/or other arteries, using electrodes that are disposed contraterally to one another, with respect to the artery, causes an increase in the tension in the arterial wall, i.e., the artery contracts.

Thus, for some applications of the invention, an artery is constricted by driving a current into the artery via electrodes that are disposed contralaterally to each other, with respect to the artery. Alternatively or additionally, an artery is dilated by driving a current into the artery via electrodes that are disposed ipsilaterally to each other, with respect to the artery. For example, in order to apply peristaltic dilation techniques to a subject's artery (e.g., as described in US 2009/0198308 to Gross, which is incorporated herein by reference), current is driven into the artery via electrodes that are disposed ipsilaterally to each other, with respect to the artery.

Figure 7A:
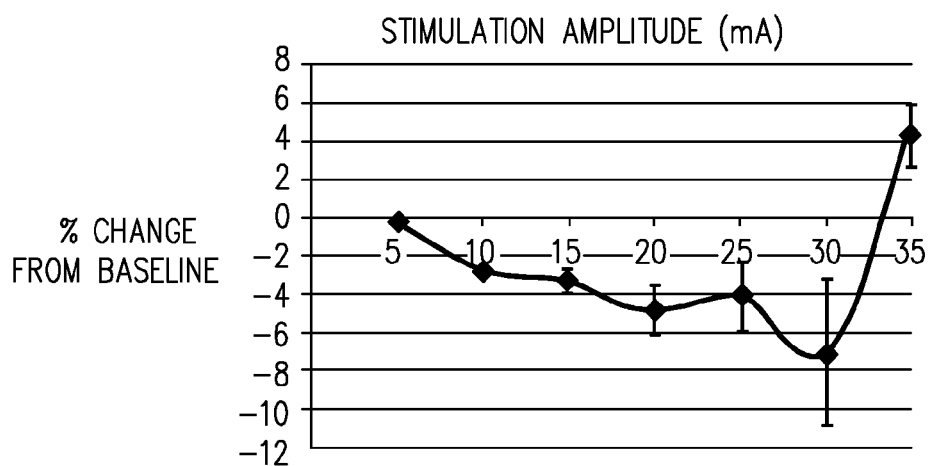
FIGS. 7A-C are graphs showing the tension that was measured in the aortic ring during stimulation of the ring with the ipsilaterally disposed electrodes using respective stimulation parameters.
Figure 7B:
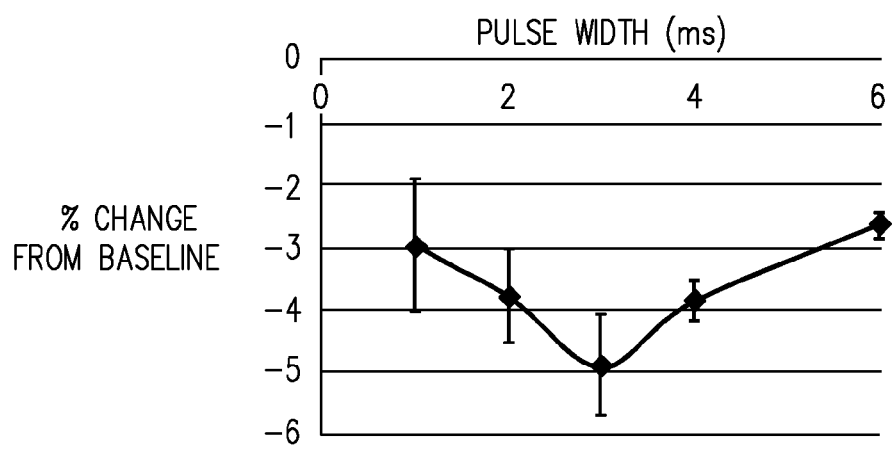
Figure 7C:
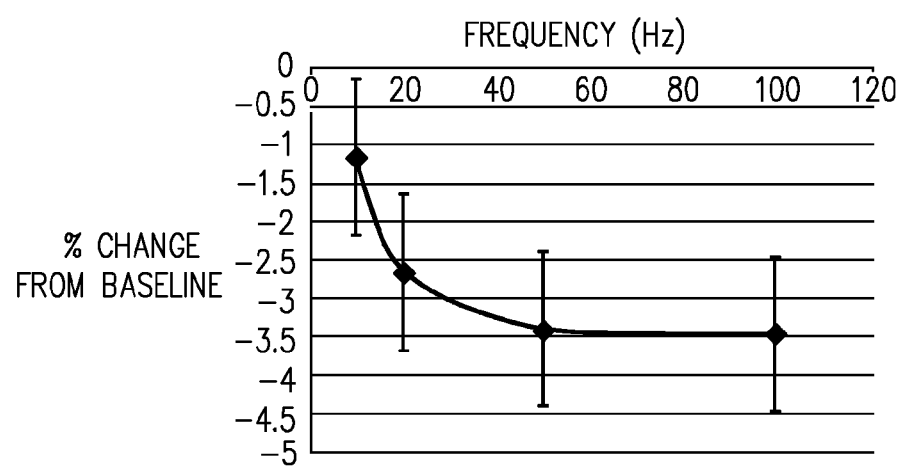

Reference is now made to FIGS. 7A-C, which are graphs showing the tension that was measured in aortic ring 80 during stimulation of the ring with ipsilateral electrodes 88, using respective stimulation parameters.

FIG. 7A is a graph showing the change in the tension measured in aortic ring 80 relative to the pre-stimulation tension in the ring, during stimulation of the ring with a current having a pulse width of 4 ms, and a frequency of 50 Hz, over a range of amplitudes. It may be observed that the greatest decrease in the tension in the ring was for currents having amplitudes of more than 15 mA, and/or less than 35 mA (e.g., 15 mA-35 mA), for example, more than 25 mA, and/or less than 33 mA (e.g., 25 mA-33 mA).

FIG. 7B is a graph showing the change in the tension measured in aortic ring 80 relative to the pre-stimulation tension in the ring, during stimulation of the ring with a current having an amplitude of 15 mA, and a frequency of 50 Hz, for a range of pulse widths. It may be observed that the greatest decrease in the tension in the ring was for currents having pulse widths of more than 1 ms, and/or less than 5 ms (e.g., 1 ms-5 ms), for example, more than 2 ms, and/or less than 4 ms (e.g., 2 ms-4 ms).

FIG. 7C is a graph showing the change in the tension measured in aortic ring 80 relative to the pre-stimulation tension in the ring, during stimulation of the ring with a current having a pulse width of 4 ms, and an amplitude of 15 mA, for a range of frequencies. It may be observed that the greatest decrease in the tension in the ring was for currents having a frequency of more than 20 Hz (e.g., more than 50 Hz), for example, 20 Hz-100 Hz.

Thus, for some applications, a subject is identified as suffering from a condition, which may be at least partially treated by causing blood vessels of the subject to dilate (e.g., by causing an artery of the subject to peristaltically dilate, as described in US 2009/0198308 to Gross and US 2009/0198097 to Gross, both of which applications are incorporated herein by reference). In response to the identification, electrodes are placed in contact with the subject's blood vessel such that the electrodes are disposed ipsilaterally to each other, with respect to the blood vessel, in accordance with the results shown in FIG. 6A. For example, the electrodes may be disposed on the same side of the inner surface of a ring that is placed around the blood vessel. Or, the electrodes may be disposed on wire frame 28 (FIG. 1A), or on catheter 52 (FIG. 3B), such that the electrodes are placed in contact with the blood vessel ipsilaterally to each other, with respect to the blood vessel.

For some applications, a current having one or more of the following parameters is driven via the electrodes, in order to cause dilation of a blood vessel of the subject, in accordance with the results shown in FIGS. 7A-C:

- an amplitude of more than 15 mA, and/or less than 35 mA (e.g., 15 mA-35 mA), for example, more than 25 mA, and/or less than 33 mA (e.g., 25 mA-33 mA);
- a pulse width of more than 1 ms, and/or less than 5 ms (e.g., 1 ms-5 ms), for example, more than 2 ms, and/or less than 4 ms (e.g., 2 ms-4 ms); and/or
- a frequency of more than 20 Hz (e.g., more than 50 Hz), for example, 20 Hz-100 Hz.

For some applications, a subject is identified as suffering from a condition, which may be at least partially treated by causing blood vessels of the subject to constrict. In response to the identification, electrodes are placed on the subject's blood vessel such that the electrodes are disposed contralaterally to each other, with respect to the blood vessel, in accordance with the results shown in FIG. 6B. For example, the electrodes may be disposed on opposite sides of the inner surface of a ring that is placed around the blood vessel. Or, the electrodes may be disposed on wire frame 28 (FIG. 1A), or on catheter 52 (FIG. 3B) such that the electrodes are placed in contact with the blood vessel, contralaterally with respect to one another.

Figure 8A:
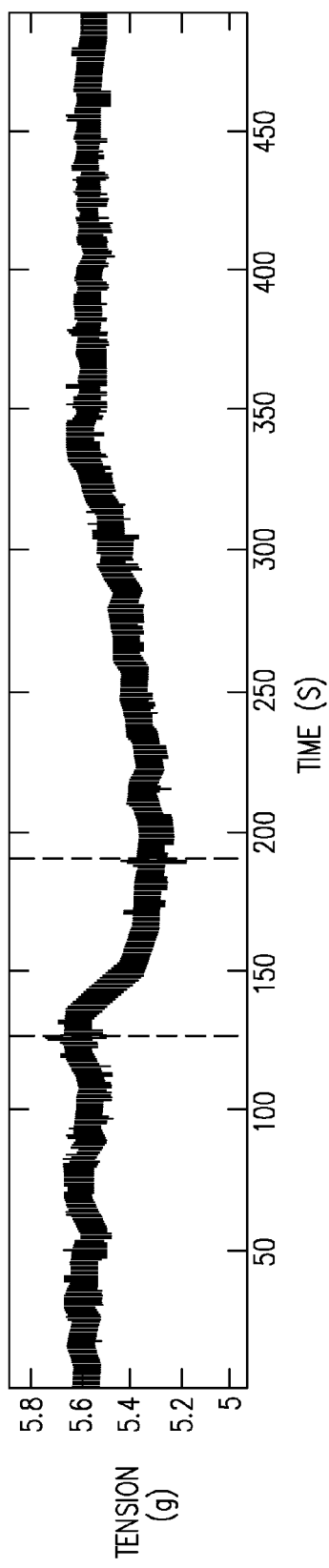

Reference is now made to FIGS. 8A-D, which are graphs showing the tension measured in aortic ring 80 in response to electrical stimulation (FIGS. 8A-B), and in response to the administration of substance P neuropeptide (FIGS. 8C-D).

FIG. 8A is a graph showing the tension measured in an aortic ring measured before, during, and after stimulation of the ring with ipsilateral electrodes using a current having an amplitude of 15 mA, a frequency of 50 Hz, and a pulse width of 4 ms. The beginning and end of the stimulation period is denoted by the vertical dashed lines on FIG. 8A.

Figure 8B:
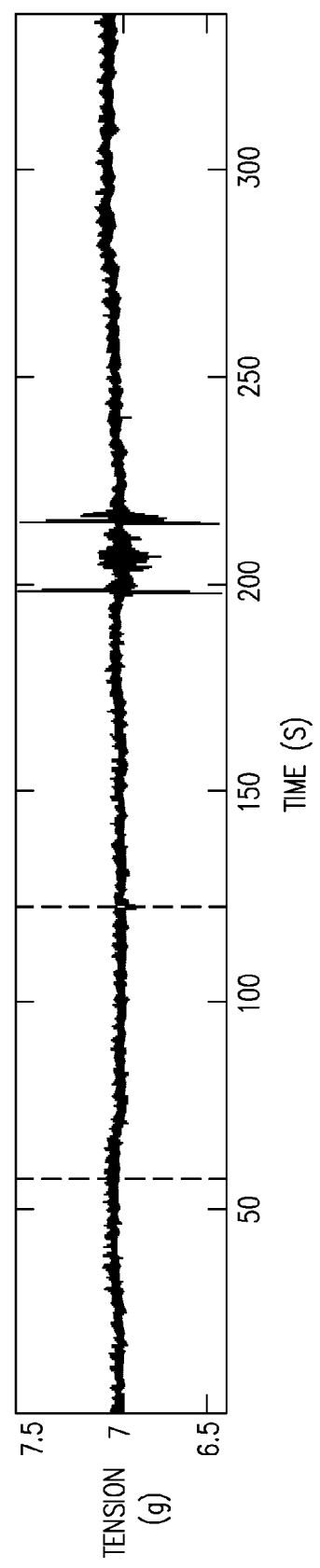

FIG. 8B shows the tension measured in an aortic ring before, during, and after stimulation of the ring with ipsilateral electrodes using a current having an amplitude of 15 mA, a frequency of 50 Hz, and a pulse width of 4 ms. Before stimulating the aortic ring to collect the data shown in FIG. 8B, the endothelial wall of the aortic ring was mechanically denuded. The beginning and end of the stimulation period is denoted by the vertical dashed lines on FIG. 8B.

FIG. 8C is a graph showing the tension measured in an aortic ring measured before, and after administration of substance P neuropeptide to the aortic ring. The time at which the substance P was administered is denoted by the downward-pointing arrow in FIG. 8C.

FIG. 8D is a graph showing the tension measured in an aortic ring measured before, and after administration of substance P neuropeptide to the aortic ring. The time at which the substance P was administered is denoted by the downward-pointing arrow in FIG. 8D. Before stimulating the aortic ring and collecting the data shown in FIG. 8D, the endothelial wall of the aortic ring was mechanically denuded.

It may be observed that electrical stimulation of the aortic ring before the endothelial denuding, resulted in the aortic ring having reduced tension, as demonstrated by FIG. 8A. Subsequent to the endothelial denuding, electrical stimulation of the aortic ring did not cause a reduction in the tension in the aortic ring. Similarly, administration of substance P caused a reduction in the tension of the aortic ring before the endothelial denuding (as demonstrated by FIG. 8C), but did not cause a reduction in the tension of the aortic ring subsequent to the endothelial denuding (as demonstrated by FIG. 8D).

Substance P is a vasodilator. Substance-P-induced vasodilation has been shown to be dependent on the release of nitric oxide from the endothelium (c.f. "In vivo measurement of endothelium-dependent vasodilation with substance P in man," Bossaller, Herz. 1992 October; 17(5):284-90). This explains the data shown in FIGS. 8C-D, namely, that substance P was effective at reducing tension in the aortic ring before the endothelial denuding, but not subsequent to the endothelial denuding.

In view of the above, the data shown in FIGS. 8A-B, indicate that the mechanism by which electrical stimulation of the aortic ring causes the aortic ring to dilate is at least partially due to the release of endothelium-derived nitric oxide NO. Thus, subsequent to endothelial denuding, electrical stimulation is not effective to dilate the aortic ring.

It is to be understood that whereas some embodiments describe the generation of peristaltic waves both upstream and downstream of a bifurcation, other embodiments of the present invention include generating a peristaltic wave on one side of the bifurcation, and generating a non-peristaltic contraction on the other side of the bifurcation, in order to increase blood pressure at the bifurcation and divert blood to the adjacent blood vessel and/or enhance blood flow through the blood vessel undergoing the contraction. Similarly, two non-peristaltic contractions may be created, on either side of the bifurcation, in order to increase blood pressure at the bifurcation and divert blood to the adjacent blood vessel.

It is to be understood that various techniques are shown and described for bringing electrodes to a desired site for application of current thereto, and that other techniques, whether for example transcatheter, laparoscopic, or open surgical, are within the scope of the present invention.

It is noted that whereas some embodiments of the present invention are described hereinabove with respect to a wire frame being used to support electrodes, the scope of the present invention includes other supports as well, such as stents. Alternatively or additionally, other techniques are used for placing the electrodes in a desired site, such as suturing.

It is noted that whereas some embodiments of the present invention are described hereinabove, according to which blood diverting device 10 is used in specific arteries and veins, the scope of the present invention includes applying the method and apparatus described herein to any arteries or veins within a subject's body, e.g., the first or the second blood vessel may be the femoral artery, or the femoral vein.

Techniques described hereinabove for enhancing flow to a second blood vessel can be practiced in combination with counterpulsation techniques and/or other techniques, such as those described in one or more of the following applications, all of which are incorporated herein by reference:

US 2008/0215117 to Gross
US 2009/0198097 to Gross
US 2009/0198308 to Gross

It is noted that embodiments of the present invention which include inducing contraction of a blood vessel do not necessarily completely occlude the blood vessel, but may only cause a decrease in diameter of the blood vessel. Alternatively, transient occlusion of the blood vessel may be induced, typically in intermittent cardiac cycles or in every cardiac cycle for an appropriate time period.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    a mechanical support element having a proximal portion and a distal portion, both portions configured to be placed inside a blood vessel of a subject;
    a first set of electrodes, disposed in series along the proximal portion of the support element, each electrode disposed at a longitudinal distance from an adjacent one of the electrodes that is less than 30 mm;

a second set of electrodes, disposed in series along the distal portion of the support element, each electrode in the second set of electrodes disposed at a longitudinal distance, from an adjacent electrode in the second set of electrodes, that is less than 30 mm,
- a distal-most electrode in the first set of electrodes and a proximal-most electrode in the second set of electrodes being disposed along the support element at a longitudinal distance from one another of more than 1 cm,
- the mechanical support element being configured to support the first and second sets of electrodes inside the blood vessel, such that the first and second sets of electrodes are brought into direct contact with a wall of the blood vessel; and a control unit configured to drive current into the blood vessel wall via the first and second sets of electrodes, wherein the blood vessel includes a first blood vessel, from which a second blood vessel bifurcates at a bifurcation, and wherein the mechanical support element is configured to bring the first set of electrodes into contact with the blood vessel wall on a first side of the bifurcation, and to bring the second set of electrodes into contact with the blood vessel wall on a second side of the bifurcation, and wherein the control unit is configured to divert blood from the first blood vessel to the second blood vessel, by driving the current into the blood vessel wall via the first and second sets of electrodes.

2. The apparatus according to claim 1, wherein a diameter of the support element is less than 35 mm.

3. The apparatus according to claim 1, wherein the support element comprises a catheter.

4. The apparatus according to claim 1, wherein the support element comprises a wire frame.

5. The apparatus according to claim 1, wherein the control unit is configured to divert blood from the first blood vessel to the second blood vessel, by generating waves of contraction in the blood vessel wall, by driving the current into the blood vessel wall via the first and second sets of electrodes.

* * * * *